US010898537B2

(12) United States Patent
Gabriele et al.

(10) Patent No.: US 10,898,537 B2
(45) Date of Patent: Jan. 26, 2021

(54) TRANSDERMAL FORMULATIONS FOR DELIVERY OF CAPSAICINOIDS

(71) Applicant: DELIVRA INC., Burlington (CA)

(72) Inventors: Joseph Gabriele, Stoney Creek (CA); Mikaela Teris, Montreal (CA); David Baranowski, Mount Stewart (CA); Beth Buchanan, Charlottetown (CA)

(73) Assignee: Delivra Inc., Burlington (CA)

( * ) Notice: Subject to any disclaimer, the term of this patent is extended or adjusted under 35 U.S.C. 154(b) by 328 days.

(21) Appl. No.: 15/749,152

(22) PCT Filed: Jul. 29, 2016

(86) PCT No.: PCT/CA2016/050899
§ 371 (c)(1),
(2) Date: Jan. 31, 2018

(87) PCT Pub. No.: WO2017/020125
PCT Pub. Date: Feb. 9, 2017

(65) Prior Publication Data
US 2018/0221427 A1 Aug. 9, 2018

Related U.S. Application Data

(60) Provisional application No. 62/199,522, filed on Jul. 31, 2015.

(51) Int. Cl.
A61K 36/81 (2006.01)
A61K 36/67 (2006.01)
A61K 9/00 (2006.01)
A61K 9/06 (2006.01)
A61K 31/11 (2006.01)
C07D 405/10 (2006.01)
A61K 36/185 (2006.01)
A61K 47/22 (2006.01)
C07D 311/04 (2006.01)
C07D 317/60 (2006.01)
C07D 311/18 (2006.01)
A61K 31/24 (2006.01)
A61P 17/06 (2006.01)
A61P 29/00 (2006.01)
A61P 17/04 (2006.01)

(52) U.S. Cl.
CPC ............ *A61K 36/81* (2013.01); *A61K 9/0014* (2013.01); *A61K 9/06* (2013.01); *A61K 31/11* (2013.01); *A61K 31/24* (2013.01); *A61K 36/185* (2013.01); *A61K 47/22* (2013.01); *A61P 17/04* (2018.01); *A61P 17/06* (2018.01); *A61P 29/00* (2018.01); *C07D 311/04* (2013.01); *C07D 311/18* (2013.01); *C07D 317/60* (2013.01); *C07D 405/10* (2013.01)

(58) Field of Classification Search
CPC .................. A61K 36/81; A61K 36/67

USPC .................................................. 424/760, 734
See application file for complete search history.

(56) References Cited

U.S. PATENT DOCUMENTS

| | | |
|---|---|---|
| 4,599,342 A | 7/1986 | LaHann |
| 4,681,897 A | 7/1987 | Brand |
| 4,997,853 A | 3/1991 | Bernstein |
| 5,043,323 A | 8/1991 | Bombardelli et al. |
| 5,665,378 A | 9/1997 | Davis |
| 6,239,180 B1 | 5/2001 | Robbins |
| 6,579,543 B1 | 6/2003 | McClung |
| 6,849,645 B2 | 2/2005 | Majeed et al. |
| 7,678,768 B2 | 3/2010 | Purpura |
| 7,744,932 B2 | 6/2010 | Faller |
| 7,943,166 B2 | 5/2011 | Muhammad |
| 8,158,682 B2 | 4/2012 | Sangameswaran |
| 8,263,093 B2 | 9/2012 | Muhammad |
| 8,273,390 B2 | 9/2012 | Muhammad |
| 8,367,733 B2 | 2/2013 | Burch |
| 8,420,600 B2 | 4/2013 | Burch |
| 8,535,738 B2 | 9/2013 | Collins |
| 8,685,381 B2 | 4/2014 | Schlessinger |
| 8,734,770 B2 | 5/2014 | Muhammad |
| 8,802,736 B2 | 8/2014 | Bucks |
| 8,889,659 B2 | 11/2014 | Bucks |
| 2005/0090557 A1* | 4/2005 | Muhammad ......... A61K 9/0014 514/627 |
| 2011/0021439 A1 | 1/2011 | Amari et al. |

(Continued)

FOREIGN PATENT DOCUMENTS

| | | |
|---|---|---|
| CA | 2510181 | 7/2004 |
| CA | 2521504 | 11/2004 |

(Continued)

OTHER PUBLICATIONS

Prausnitz, M.R., Langer, R. Transdermal Drug Delivery. Nat. Biotechnol. 2008, 26(11):1261-1268.

(Continued)

Primary Examiner — Michael Barker
Assistant Examiner — Deborah A Davis
(74) Attorney, Agent, or Firm — Snell & Wilmer L.L.P.

(57) ABSTRACT

The present application is directed to transdermal formulations comprising one or more capsaicinoids, one or more 1,4-dialdehyde sesquiterpenes, a penetration enhancer comprising tetrahydropiperine and a transdermal formulation base. The formulations advantageously show improved color characteristics and cause less irritation compared to other known transdermal or topica formulations comprising capsaicinoids.

19 Claims, 10 Drawing Sheets

(56) References Cited

U.S. PATENT DOCUMENTS

| | | | | |
|---|---|---|---|---|
| 2011/0038965 | A1* | 2/2011 | McKay | A61K 36/30 424/742 |
| 2014/0227342 | A1 | 8/2014 | Farber | |
| 2014/0271923 | A1 | 9/2014 | Reid | |

FOREIGN PATENT DOCUMENTS

| | | |
|---|---|---|
| CA | 2684601 | 10/2008 |
| EP | 1874132 | 1/2008 |
| EP | 2629610 | 8/2013 |
| IN | 2299/MUM/2008 | 10/2008 |
| WO | WO2006058140 | 6/2006 |
| WO | WO2009127992 | 10/2009 |
| WO | WO2010151653 | 12/2010 |
| WO | WO2012060845 | 5/2012 |
| WO | WO2014130922 | 8/2014 |

OTHER PUBLICATIONS

Gilboe, L. et al. "Assessment of Mechanisms Involved in Antinociception Caused by Sesquiterpene Polygodial". The Journal of Pharmacology and Experimental Therapeutics. 292(1):164-172, 2000.

Pongpiriyadacha, Y. et al. "Protective Effects of Polygodial on Gastric Mucosal Lesions Induced by Necrotizing Agents in Rats and the Possible Mechanisms of Action". Biol. Pharm. Bull. 26(5):651-657, 2003.

Parashar, B. et al. "Natural Therapy of Fungal Nail Disease: Review". The Pharma Journal, 1(4):46-60, 2012.

Escalera, J. et al. TRP1 Mediates the Noxious Effects of Natural Sesquiterpene Deterrents. Journal of Biological Chemistry, 283(35):24136-24143, 2008.

Shivanand, P. et al. "Phytosomes: Technical Revolution in Phytomedicine". International Journal of PharmTech Research. 2(1): 627-631, 2010.

Agrawal, V.K. et al. "Improvement in Bioavailbility of Class-III Drug: Phytolipid Delivery System". International Journal of Pharmacy and Pharmaceutical Sciences. 4(1):37-42, 2012.

Williams, A.C. et al. "Penetration Enhancers". Advanced Drug Delivery Reviews. 64:128-137, 2012.

Prausnitz, M.R. et al. "Skin Barrier and Transdermal Drug Delivery". Medical Therapy. Section 19:2065-2073. 2012.

Ghanbarzadeh, Saeed et al. "Enhanced Transdermal Delivery of Dicofenac Sodium via Conventional Liposimes, Ethosomes, and Transfersomes". BioMed Research International. vol. 2013:1-7, 2013.

Ghosh, Indrajit et al. Influence of Critical Parameters of Nanosuspension Formulation on the Permeability of a Poorly Soluble Drug Through the Skin-ACase Study. American Association of Pharmaceutical Scientists. 14(3):1108-1117, 2013.

* cited by examiner

A

B

C

D

TRANSDERMAL FORMULATIONS FOR DELIVERY OF CAPSAICINOIDS

CROSS REFERENCE TO RELATED APPLICATIONS

This is a national stage application of PCT/CA2016/050899, filed Jul. 29, 2016, which claims priority from U.S. Provisional patent application serial number 62/199,522, filed Jul. 31, 2015, all of which are incorporated herein by reference in their entirety.

FIELD

The present application describes transdermal formulations for delivery of active agents. In particular, the present formulations provide for the effective transdermal delivery of capsaicinoids.

BACKGROUND

The premature metabolism of drugs as a result of the first-pass effect has made transdermal delivery an attractive and alternative strategy (Prausnitz, M. R., Langer, R. "Transdermal Drug Delivery. *Nat. Biotechnol.* 2008, 26(11): 1261-1268). For many years, people have placed natural substances on the skin for local ailments. However, lending this strategy towards all therapeutic drugs is not feasible. The human skin acts as a formidable barrier due in large part to the stratum corneum, which mostly consists of a lipid-enriched matrix and blocks entry of most topically applied agents, with the exception of low molecular weight, lipid-soluble drugs. This poses a challenge for administrating medications via the skin for either local cutaneous or systemic therapy.

Transdermal drug delivery strategies have thus focused primarily on the manipulation of this lipid milieu. In particular, penetration enhancers which interact with skin constituents to promote drug transport have provided an approach to increase the range of therapeutic agents that can be delivered.

Despite the significant permeability barrier of the stratum corneum, drug delivery via the skin is a very attractive option and is widely employed for both local and systemic therapy. Topical treatment of cutaneous disorders obviously targets the site of disease, thereby minimizing adverse side effects elsewhere within the body. Delivery of systemic therapies via the skin avoids degradation of the medication within the gastrointestinal tract and first-pass metabolism by the liver, both of which are associated with oral administration of drugs, in addition to evading the pain and safety issues associated with injections. Transdermal delivery of drugs, in some cases, enables infrequent dosing and maintenance of steady state drug levels.

Capsaicin has been topically delivered for the treatment of pain (including painful neuropathies and musculoskeletal pain), inflammation, itch, psoriasis and pruritis and as a general anti-irritant. However, the topical delivery of capsaicin is known to be associated with a burning sensation which has limited its use.

SUMMARY

The present application includes transdermal formulations for the delivery of capsaicinoids to a subject. In some embodiments, the transdermal formulations reduce the burning sensation and irritation that is associated with prior topical or transdermal capsaicin formulations. In some embodiments, the transdermal formulations have improved color characteristics.

In the present application, it has been shown that the penetration of a capsaicinoid compound is enhanced in the presence of a penetration enhancer comprising tetrahydropiperine and in the presence of a source of polygodial and in a transdermal delivery base. This improved penetration was not seen with the penetration enhancer and capsaicinoid on its own (i.e. in the absence of the source polygodial and in the absence of the transdermal delivery base) or in the presence of different penetration enhancers. Further, it was shown that the transdermal formulations of the application had reduced irritation characteristic (for e.g. burning sensations and other skin irritations or erythema) compared to other known transdermal formulations comprising capsaicinoids. Finally it was shown that the resulting transdermal formulation had improved colour characteristics.

In some embodiments, the transdermal formulations of the application comprise one or more capiscinoinds, one or more 1,4-dialdehyde sesquiterpenes, a penetration enhancer comprising tetrahydropiperine and a transdermal formulation base.

The present application includes methods for treating one or more capsaicinoid-responsive conditions comprising administering an effective amount of a transdermal formulation of the application to a subject in need thereof. In some embodiments the capsaicinoid-responsive conditions are selected from one or more of pain (including painful neuropathies and musculosketal pain), inflammation, itch, psoriasis, pruritis and microbial infections. In some embodiments, the formulations of the present application advantageously provide treatment with a lower amount of irritation or burning sensation compared to other transdermal or topical capsaicinoid formulations. This allows the formulations of the application to be applied to sensitive areas, such as around diabetic and open wounds, around the eyes and/or around the genital area.

In some embodiments of the application, the formulations described herein have improved color charactistics. By improved characteristics it is meant that the formulation is lighter in colour than other transdermal formulations comprising capsaicinoids.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1(*a*)-(*d*) are photos of formulation color characteristics (a) capsaicin; (b) formulation of the application; (c) rutin; and (d) formulation of the application.

μg/mL), capsaicin with equimass THP (5 μg/mL), or capsaicin with equimass DMI (5 μg/mL). The concentration of capsaicin at 2.0, 2.5, and 5.0 hours alone (34, 34, 460 ng/mL), with THP (18, 139, 580 ng/mL), or DMI (156, 258, 535 ng/mL) did not demonstrate statistically significant results. Error bars depicted are standard deviation.

Figure 4:
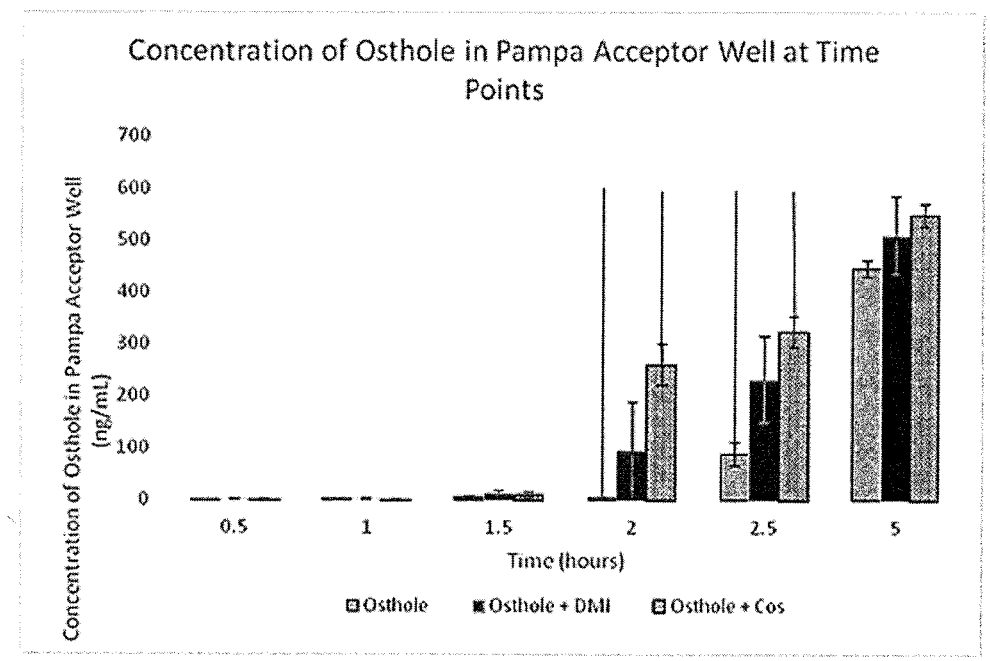

FIG. 4 is a bar graph showing the effect of natural and synthetic penetration enhancers on the permeation of osthole in the PAMPA system. Osthole concentration was quantified in the acceptor well at various timepoints after loading the donor compartment with osthole alone (5 μg/mL), osthole with equimass THP (5 μg/mL), or osthole with equimass DMI (5 μg/mL). The concentration of osthole at 2.0, 2.5, and 5.0 hours alone (4, 89, 445 ng/mL), with THP (261, 324, 549 ng/mL), or DMI (95, 232, 510 ng/mL) demonstrate significance for the enhancer THP at 2.0 and 2.5 hours (*, P values=0.0115, 0.0120) only. Error bars depicted are standard deviation.

Figure 5:
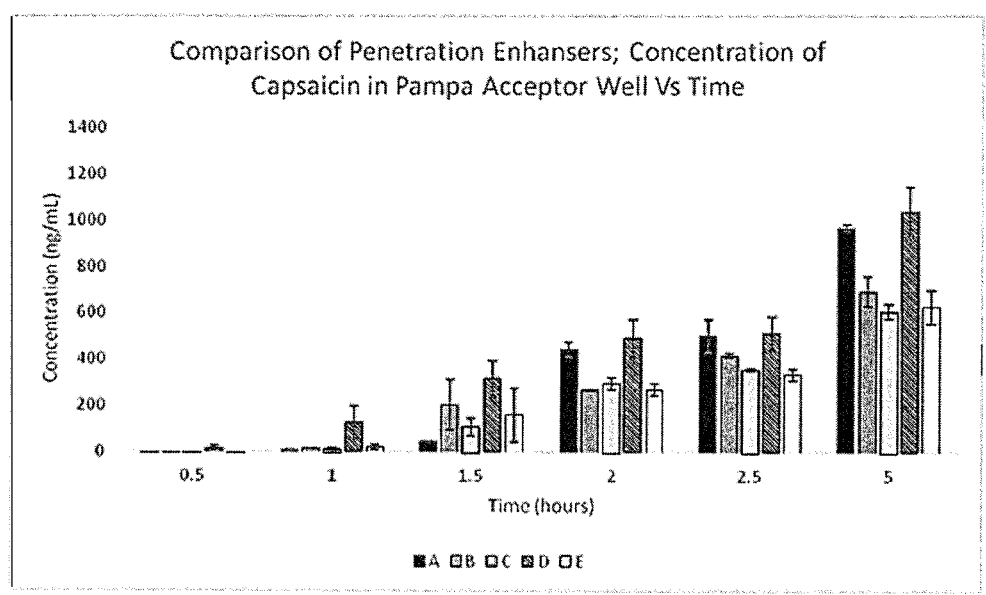

FIG. 5 is a bar graph showing the effect of natural penetration enhancers on the permeation of capsaicin in the PAMPA system. Capsaicin concentration was quantified in the acceptor well at various timepoints after loading the donor compartment (5ug/mL) with capsaicin "alone" (A), with equimass polygodial (B), with equimass TMP (C), with equimass THP (D) or a combination of equimass TMP and THP (E). No statistical enhancement was measured. Significant suppression of penetrance was observed fat 5 hours for TMP and TMP+THP (Pvalue<0.05). Error bars depicted are standard deviation.

Figure 6:
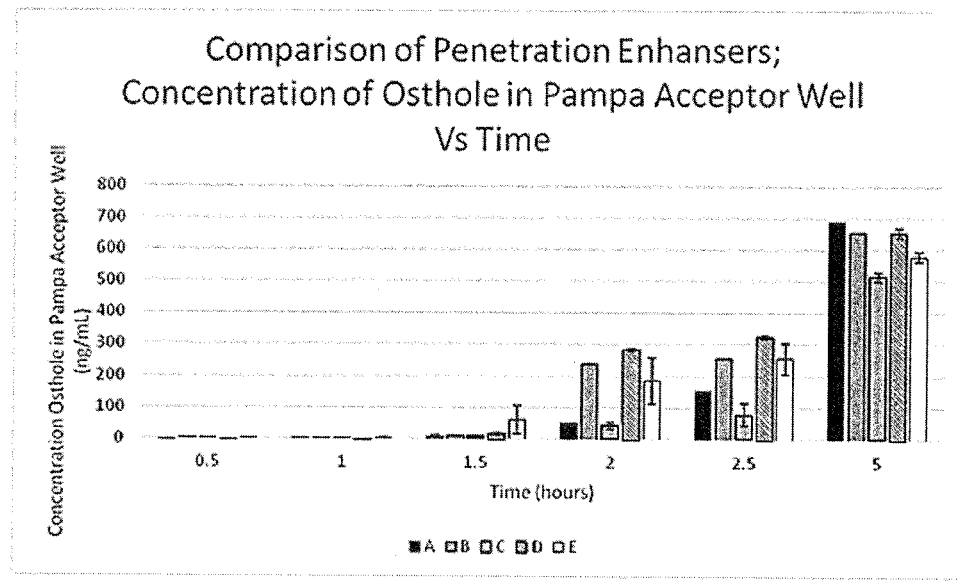

FIG. 6 is a bar graph showing the effect of natural penetration enhancers on the permeation of osthole in the PAMPA system. Osthole concentration was quantified in the acceptor well at various timepoints after loading the donor compartment (5ug/mL) with osthole "alone" (A), with equimass polygodial (B), with equimass TMP (C), with equimass THP (D) or a combination of equimass TMP and THP (E). Statistical enhancement was measured for THP compared to osthole alone at 2 hours (*, Pvalue=0.0058). Error bars depicted are standard deviation.+note single points were used for set B due to problem with the assay and therefore error bars not shown. Error bars depicted are standard deviation.

Figure 7:
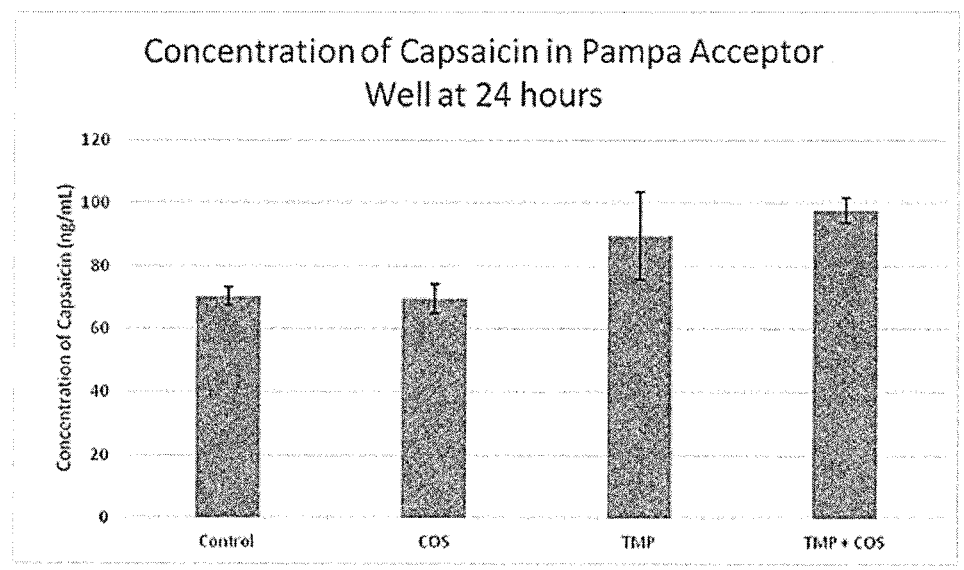

FIG. 7 is a bargraph showing the effects of penetration enhancers in formulations of capsaicin in exemplary base formulations of the application. Capsaicin concentration was quantified in the acceptor well at various timepoints loading the donor compartments with each formulation. All formulations contain capsaicin (Capsicum annum L. (Solanacea), Cayanne 0.025% w/w) alone (Control), with 1.0% w/w TMP (TMP), with 0.1% w/w THP (THP), and 2.0% w/w TMP and 0.1% THP (TMP+THP). Only TMP+THP highlighted a statistically significant enhancement (*, P value=0.0006). Error bars depicted are standard deviations.

Figure 8:
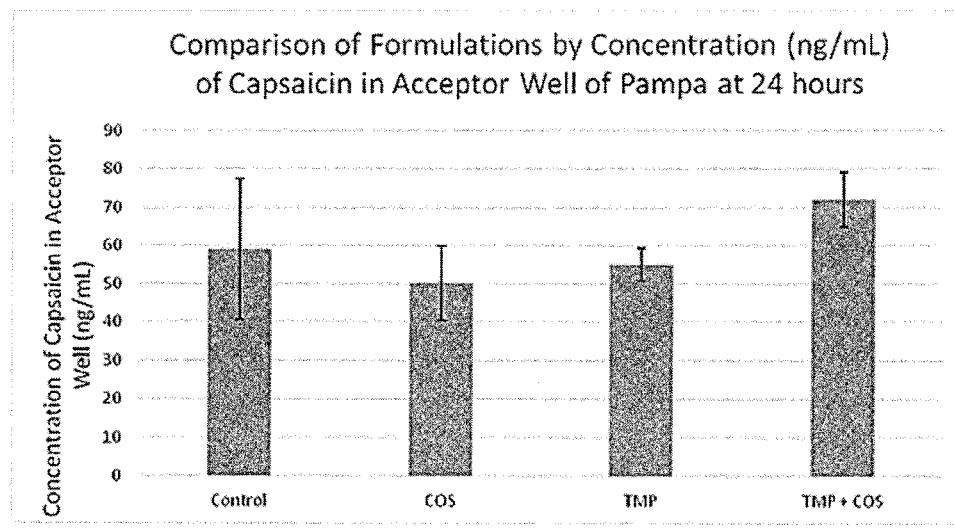

FIG. 8 is a bar graph showing a repetition of the effects of penetration enhancers in formulations of capsaicin in exemplary base formulations of the application. Capsaicin concentration was quantified in the acceptor well at various timepoints after loading the donor compartments with each formulation. All formulations contain capsaicin (Capsicum annum L. (Solanacea), Cayanne 0.025% w/w) alone (Control), with 1.0% w/w TMP (TMP), with 0.1% w/w THP (THP), and 2.0% w/w TMP and 0.1% THP (TMP+THP). In this data set a trend for improved penetration in the presence of TMP+THP was observed. Error bars depicted are standard deviations.

Figure 9:
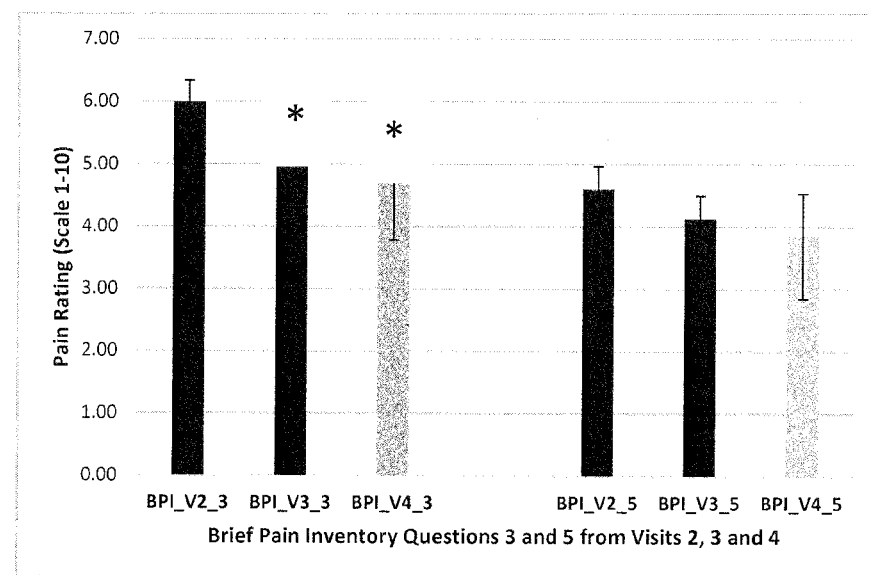

FIG. 9 is a bar graph showing responses to the Brief Pain Inventory Questionnaire after topical administration of an exemplary formulation of the application for patients suffering from joint pain after 3 and 4 weeks after a baseline visit.

Figure 10:
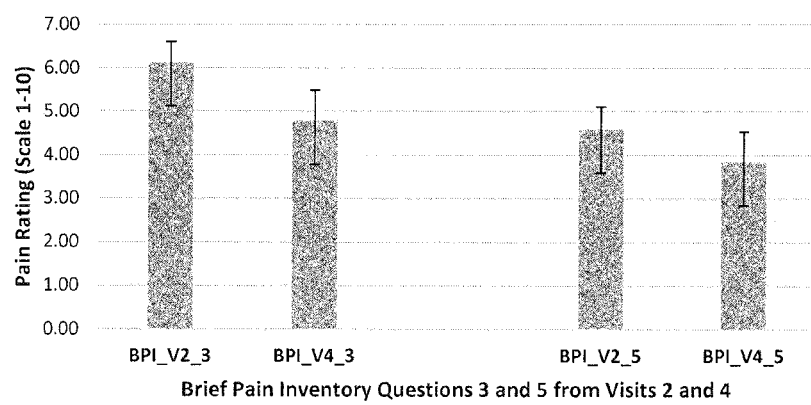

FIG. 10 is a bar graph showing responses to the Brief Pain Inventory Questionnaire after topical administration of an exemplary formulation of the application for patients suffering from joint pain after 4 weeks after a baseline visit.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The present description refers to a number of chemical terms and abbreviations used by those skilled in the art. Nevertheless, definitions of selected terms are provided for clarity and consistency.

As used in this application, the singular forms "a", "an" and "the" include plural references unless the content clearly dictates otherwise. For example, an embodiment including "an agent" should be understood to present certain aspects with one agent or two or more additional agents.

In embodiments comprising an "additional" or "second" component, such as an additional or second agent, the second component as used herein is chemically different from the other components or first component. A "third" component is different from the other, first, and second components, and further enumerated or "additional" components are similarly different.

The term "agent" as used herein indicates a compound or mixture of compounds that, when added to a formulation, tend to produce a particular effect on the formulation's properties.

The term "active agent" or "active pharmaceutical ingredient" or "API" as used herein means an agent or a mixture of agents that causes the desired therapeutic effect.

The term "buffering agent" as used herein refers to a compound or mixture of compounds that adjusts the pH of the formulation.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific process step to be performed, and the identity of the compounds involved, but the selection would be well within the skill of a person trained in the art. All process/method steps described herein are to be conducted under conditions sufficient to provide the desired transformation. A person skilled in the art would understand that all process conditions, including, for example, solvent, time, temperature, pressure, component ratio and whether or not the step should be performed under an anhydrous or inert atmosphere, can be varied to optimize the yield of the desired product and it is within their skill to do so.

"Formulation" and "pharmaceutical formulation" as used herein are equivalent terms referring to a formulation for pharmaceutical use.

The term "pharmaceutically acceptable" means compatible with the treatment of animals, in particular, humans.

The term "effective amount" as used herein means an amount sufficient to achieve the desired result and accordingly will depend on the ingredient and its desired result. Nonetheless, once the desired effect is known, determining the effective amount is within the skill of a person skilled in the art.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, prevention of disease spread, delaying or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. Treatment methods comprise administering to a subject a therapeutically effective amount of an active agent and optionally consists of a single administration, or alternatively comprises a series of applications. The length of the treatment period depends on a variety of factors, such as the severity of the condition, the age of the patient, the concentration of active ingredient or agent, the activity of the compositions described herein, and/or a combination thereof. It will also be appreciated that the effective dosage of the agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

"Topical composition" as used herein includes a composition that is suitable for topical application to the skin, nail, mucosa, wound bed or wound cavity. A topical composition may, for example, be used to confer a therapeutic or cosmetic benefit to its user. Specific topical compositions can be used for local, regional, or transdermal application of substances.

The term "topical administration" is used herein to include the delivery of a substance, such as a therapeutically active agent, to the skin or a localized region of the body.

"Transdermal" as used herein includes a process that occurs through the skin. The terms "transdermal," "percutaneous" and "transcutaneous" can be used interchangeably. In certain embodiments, "transdermal" also includes epi cutaneous. Transdermal administration is often applied where systemic delivery of an active is desired, although it may also be useful for delivering an active to tissues underlying the skin with minimal systemic absorption.

"Transdermal application" as used herein includes administration through the skin. Transdermal application can be used for systemic delivery of an active agent; however, it is also useful for delivery of an active agent to tissues underlying the skin with minimal systemic absorption. In certain embodiments, "transdermal application" can also include epicutaneous application.

The term "emollient" as used herein refers to a compound or mixture of compounds that adds or replaces natural oils in the skin, for example by maintaining the integrity of the hydrolipids of the skin.

The term "polar emollient" as used herein refers to emollient compounds, which are generally oils, having heteroatoms that differ in electronegativity. This results in a dipole moment. Typical polar oils are fatty alcohols, esters and triglycerides. While they are still water insoluble and oil-loving, these oils have unique characteristics due to their polar nature. They typically combine with higher hydrophobic lipid balance (HLB) emulsifiers to make stable emulsions, they dissolve materials that are insoluble in nonpolar oils, and they provide unique properties when compared with nonpolar oils such as mineral oil.

The term "medium polar emollient" as used herein refers to emollient compounds, which are generally oils, that are less polar than the polar emollients but still more polar than nonpolar oils such as mineral oil.

The term "humectant" as used herein refers to a compound or mixture of compounds intended to increase the water content of the top layers of skin.

The term "emulsifier" of "emulsifying agent" as used herein refers to a compound of mixture of compounds which promote or facilitate the dispersion of one substance in another to form an emulsion.

The term "penetration enhancer" as used herein refers to a compound or mixture of compounds that improves the rate of percutaneous transport of an active agent across the skin for use and delivery of active agents to organisms such as mammals.

The term "flavonoid compounds" as used herein refers to a class of plant secondary metabolites that have the general structure of a 15-carbon skeleton, which contains two phenyl rings (A and B) and heterocyclic ring (C). The basic chemical structure of a flavonoid as used herein is as follows:

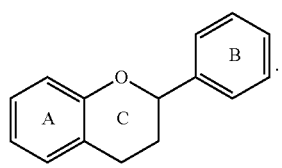

However, the term flavonoid includes the following flavonoids:

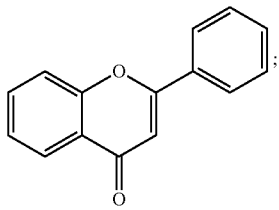 [SMILES: O=c1cc(-c2ccccc2)oc2ccccc12]

isoflavonoids:

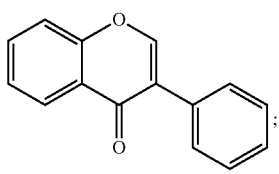 [SMILES: O=c1c(-c2ccccc2)coc2ccccc12]

and neoflavonoids:

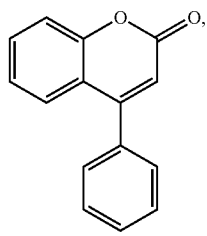 [SMILES: O=c1cc(-c2ccccc2)c2ccccc2o1]

as well as their non-ketone containing counterparts, know as flavanoids. Flavonoids are one of the largest known nutrient families, and include over 6,000 already-identified family members. Some of the best-known flavonoids include rutin, quercetin, kaempferol, catechins, and anthocyanidins. This nutrient group is most famous for its antioxidant and anti-inflammatory health benefits, as well as its contribution of vibrant color to foods.

The term "1,4-dialdehyde sesquiterpene" as used herein refers to bicyclic sequiterpenes having the drimane parent structure wherein the drimane structure comprises a 1,4-dialdehyde substitution pattern. The drimane parent structure is as follows:

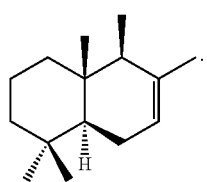

The term "polygodial" as used herein is a compound of the chemical formula:

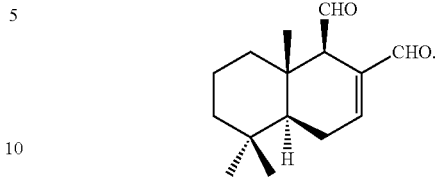

The term "capsaicinoid" as used herein refers to a family of active chemical compounds that are produced as secondary metabolites by chili peppers, which are plants belonging to the genus *Capsicum*. These compounds are known for their pungency and for producing a burning sensation when contacted with human tissue. In an embodiment the capsaicinoid is capsaicin which has the following chemical structure:

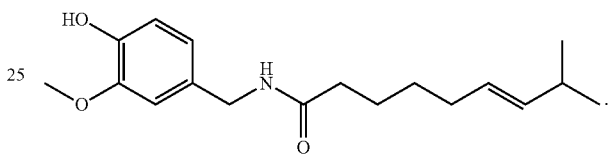

Other known natural capsaicinoids include dihydrocapsaicin, nordihydrocapsaicin, homodihydrocapsaicin, homocapsaicin and nonivamide. A known non-natural capsaicinoid is the vanillylamide of n-nonanoic acid (also known as VNA or PAVA).

The term "polygodial source" as used herein refers to a natural product or natural product extract that contains polygodial as an active constituent. Polygodial is an active constituent of Dorrigo Pepper, Mountain Pepper, Horopito, Canelo, Paracress and Water-pepper. In some embodiments the polygodial source is Mountain Pepper, such as Tazmanian Mountain Pepper (TMP) or *Tasmannia lanceolata*.

The term "capsaicinoid source" as used herein refers to a natural product or natural product extract that contains at least one capsaicinoid as an active constituent. Capsaicinoids are an active constituent of plants of the genus, *Capsicum*, such as chili peppers or cayenne pepper.

The term "Cosmoperine™", "COS" or "THP" as used herein refers to the compound "tetrahydropiperine" having the following chemical structure:

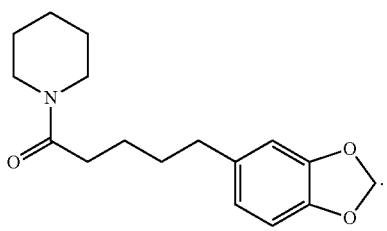 [SMILES: O=C(CCCCc1ccc2c(c1)OCO2)N1CCCCC1]

The term "wt %" means a percentage expressed in terms of weight of the ingredient or agent over the total weight of the formulation multiplied by 100.

II. Formulations of the Application

In some embodiments, the transdermal formulations of the application comprise one or more capsaicinoinds, one or more 1,4-dialdehyde sesquiterpenes, a penetration enhancer comprising tetrahydropiperine and a transdermal formulation base.

In some embodiments, the transdermal formulations of the application comprise a source of one or more capsaicinoids, a source of one or more 1,4-dialdehyde sesquiterpenes, a penetration enhancer comprising tetrahydropiperine and a transdermal formulation base.

In some embodiments, the one or more 1,4-dialdehyde sesquiterpenes are selected from polygodial, drimanial, isovelleral, warburganal and mixtures thereof. In some embodiments, the one or more 1,4-dialdehyde sesquiterpenes comprise polygodial. In some embodiments, the one or more 1,4-dialdehyde sesquiterpenes consist of polygodial. In some embodiments, the source of the one or more 1,4-dialdehyde sesquiterpenes is *Tasmannia lanceolata* or TMP. In some embodiments, the one or more 1,4-dialdehyde sesquiterpenes are provided as a *Tasmannia lanceolata* extract.

In some embodiments, the source of the one or more 1,4-dialdehyde sesquiterpenes is present in the formulation in an amount of about 1% wt % to about 5 wt %, or about 2 wt % to about 4 wt %, of the total formulation.

In some embodiments, the source of one or more capsaicinoids is chili pepper or cayenne pepper, or an extract thereof. In some embodiments, the source of one or more capsaicinoids is cayenne pepper.

In some embodiments, the source of the one or more capsaicinoids is present in the formulation in an amount of about 0.005% wt % to about 0.5 wt %, or about 0.01 wt % to about 0.1 wt %, or about 0.075 wt %, of the total formulation.

In some embodiments, the penetration enhancer comprises tetrahydropiperine. In some embodiments, penetration enhancer consists essentially of tetrahydropiperine. In some embodiments, the penetration enhancer consists of tetrahydropiperine.

In some embodiments, the tetrahydropiperine is present in the formulation in an amount of about 0.01% wt % to about 1.0 wt %, or about 0.05 wt % to about 0.5 wt %, of the total formulation In some embodiments, the transdermal formulations of the application comprise capsaicin, polygodial and tetrahydropiperine, the latter three ingredients being comprised in a transdermal formulation base.

In some embodiments, the transdermal formulations of the application comprise a source of capsaicin, a source of polygodial and tetrahydropiperine, the latter three ingredients being comprised in a transdermal formulation base.

In some embodiments, the transdermal formulations of the application comprise a TMP or an extract thereof, cayenne pepper or an extract thereof, tetrahydropiperine and a transdermal formulation base.

In some embodiments, the transdermal formulations of the application comprise, for example, a TMP or an extract thereof such as polygodial, capsaicin and THP, in a transdermal base formulation, wherein the formulation has increased penetration of capsaicin and a decreased burning sensation, when applied topically. In some embodiments, the formulation can be applied to, or near, sensitive areas of the body, such as genitals or eyes, with a decreased, or abolished, burning sensation.

In some embodiments, the transdermal formulations of the application comprise or consist of, polygodial or TMP, THP and capsaicin, in a transdermal base formulation, wherein the formulation has increased penetration of capsaicin and a decreased burning sensation, when applied topically.

In some embodiments of the application, the formulations described herein have improved color charactistics. By improved color characteristics it is meant that the formulation is lighter in color than other transdermal formulations comprising capsaicinoids (see FIG. 1).

In some embodiments of the application the formulations described herein are in the form of a cream, gel, liquid suspension, ointment, solution, patch or any other form for transdermal administration and the contents of the formulation adjusted accordingly. In some embodiments, the formulations are in the form of a cream. In some embodiments the cream has a viscosity of about 50000 cps to about 500000 cps, or about 85000 cps to about 200000 cps as measured using a Brookfield RVT T4 2 RPM instrument at room temperature.

The transdermal formulation base can be any such formulation currently used for the topical or transdermal delivery of active agents. Non-limiting examples of such base formulations include, Glaxal base, pluronic lethicin organogel (PLO, Murdan, Sudaxshina in Hospital Pharmacist, July/August 2005, Vol. 12, pp/267-270) etc.

In some embodiments, the transdermal formulation base comprises:
(a) an aqueous phase comprising water and at least one emulsion stabilizer;
(b) an oil phase comprising at least one emulsifier, at least one emulsion stabilizer, at least one emollient comprising at least one flavonoid, and at least one other emollient; wherein the oil and aqueous phase form an emulsion;
(c) an external phase comprising at least one flavonoid containing-extract, at least one penetration enhancer comprising tetrahyropiperine, at least one capsaicinoind, at least one 1,4-dialdehyde sesquiterpene and at least one phospholipid-complexed flavonoid; and optionally
(d) at least one preservative phase.

In some embodiments, the transdermal formulation comprises:
(a) an aqueous phase comprising water and at least one emulsion stabilizer;
(b) an oil phase comprising at least one emulsifier, at least one emulsion stabilizer, at least one emollient comprising at least one flavonoid, and at least one other emollient; wherein the oil and aqueous phase form an emulsion;
(c) an external phase comprising at least one flavonoid containing-extract, at least one penetration enhancer comprising tetrahyropiperine, at least one capsaicinoind, polygodial or TMP and at least one phospholipid-complexed flavonoid; and optionally
(d) at least one preservative phase.

In some embodiments, the transdermal formulation base comprises an oil-in-water emulsion. In some embodiments, the formulation is a multiphase emulsion, such as an oil-in-water-oil emulsion or a water-in-oil-water emulsion.

In some embodiments, the aqueous phase comprises the water soluble emulsion stabilizer and the oil phase comprises the emulsifiers, the oil-soluble emulsion stabilizers, the polar and medium polar emollients. In some embodiments both the oil phase and the aqueous phase comprise ingredients that are stable (i.e. do not degrade to a significant extent) at a temperature of about 65° C. to about 85° C., about 70° C. to about 80° C., or about 75° C., for a time period of about 30 minutes to about 12 hours, or about 1 hour to about 6 hours. In some embodiments the external phase comprises the at least one capsaicinoind, the at least one 1,4-dialdehyde sesquiterpene, and the penetration enhancer comprising tetrahydropiperine.

Emulsifiers

In some embodiments the emulsifier is any oil-soluble fatty acid ester or mixture of fatty acid esters in which the fatty acid esters have a fatty acid composition similar to the fatty acid composition of skin for generating skin-compatible liquid crystals and to mimic the molecular organization of the intracellular lipidic laminae of the stratum corneum. Such liquid crystals are able to rapidly cross skin layers as well as to integrate into the skin's own lipid barrier to provide strength and greater integrity to this barrier.

In some embodiments the fatty acid esters are selected from sugar alcohol and fatty acid alcohol esters of any $C_{14}$-$C_{26}$-fatty acid or mixtures thereof. In some embodiments, the fatty acid esters are esters of fatty acids that are present in olive oil, palm oil and/or canola oil. In some embodiments, the fatty acids are esterified with fatty acid alcohols such as, but not limited to, cetyl alcohol, cetaryl alcohol, lauryl alcohol, stearyl alcholol, myristyl alcohol and/or oleyl alcohol. In some embodiments, the fatty acids are esterified with sugar alcohols such as, but not limited to, sorbitol, glycerol, mannitol, inositol, xylitol, erythritol, threitol, arabitol and/or ribitol. Olive oil fatty acid esters, and their use in transdermal formulations is described, for example, in U.S. Patent Application Publication No. 2011/0021439. In some embodiments, the fatty acid esters are sorbitan esters of palm oil or olive oil, such as sorbitan olivate or sorbitan palmitate. For example, sorbitan olivate is derived from fatty acids present in olive oil and esterified with sorbitol, and sorbitan palmitate is derived from fatty acids present in palm oil and esterified with sorbitol. In other embodiments, the fatty acid esters are cetearyl esters of olive oil, such as cetearyl olivate. For example, cetearyl olivate is derived from fatty acids present in olive oil and esterified with cetearyl alcohol. In further embodiments, the fatty acid esters are cetyl esters of palm oil, such as cetyl palmitate. For example, cetyl palmitate is derived from fatty acid esters present in palm oil and esterified with cetyl alcohol.

In some embodiments, the emulsifier is present in the formulations of the application in an amount of about 1 wt % to about 10 wt %, about 2 wt % to about 8 wt %, or about 4 wt % to about 6 wt %.

Emulsion stabilizers

In some embodiments, the emulsion stabilizer is any compound or mixture of compounds that helps to maintain the oil-in-water emulsion. There are three types of emulsion instability: flocculation, creaming, and coalescence. Flocculation describes the process by which the dispersed phase comes out of suspension in flakes. Coalescence is another form of instability, which describes when small droplets combine to form progressively larger ones. Emulsions can also undergo creaming, which is the migration of one of the substances to the top or bottom (depending on the relative densities of the two phases) of the emulsion under the influence of buoyancy or centripetal force when a centrifuge is used. Generally, emulsion stability refers to the ability of an emulsion to resist change in its properties over time. In the present application an emulsion stabilizer is present in both the oil phase and the aqueous phase.

In some embodiments, the emulsion stabilizer is one or more waxes. In some embodiments the waxes are selected from animal and plant waxes and mixtures thereof. In some embodiments, the plant wax is a wax derived from olives or from palm (e.g. carnauba wax). In some embodiment, the animal wax is beeswax. The one or more waxes are stabilizers that are present in the oil phase of the formulation.

In some embodiment, the oil phase emulsion stabilizer is present in the formulation in an amount of about 1 wt % to about 10 wt %, about 2 wt % to about 8 wt % or about 3 wt % to about 6 wt %.

In some embodiments, the emulsion stabilizer is one or more thickening agents. In some embodiments, the thickening agents are any compound or mixture of compounds that maintains components in the formulation in suspension and provides a suitable consistency to the formulation.

In some embodiments, the emulsion stabilizer is selected from natural polymers, gums and synthetic polymers, and mixtures thereof. In some embodiments, natural polymers, gums and synthetic polymers, and mixtures thereof, are water soluble and therefore are present in the aqueous phase of the formulation. In some embodiments, the natural polymers are selected from alginic acid and derivatives thereof, cellulose and derivatives thereof and scleroglucans, and mixtures thereof. In some embodiments, the gums are selected from xanthan gum, tara gum, guar gum and arabic gum, and mixtures thereof. In some embodiments, the synthetic polymers are selected from polyacrylates, polyisobutenes and polysorbates, and mixtures thereof.

In some embodiments, the aqueous phase emulsion stabilizer is present in the formulations of the application in an amount of about 0.1 wt % to about 1 wt %, about 0.2 wt % to about 0.8 wt %, or about 0.4 wt % to about 0.6 wt %.

Emollient Comprising at Least One Flavonoid

In some embodiments, the one or more emollients comprising one or more flavonoid compounds are polar emollients. Polar emollients generally include natural oils and extracts from plants. In some embodiments, the polar emollients are derived from fruits (including berries), vegetables, herbs, spices, legumes, leaves, seeds and/or grains. In some embodiments, the polar emollient is a natural oil or extract from citrus, *Ginkgo biloba*, tea, wine, cacao, onion, kale, parsley, red beans, broccoli, endive, celery, cranberries, blackberries, red raspberries, blackcurrants, acai, blueberries, bilberries, milk thistle, apples, hawthorn, *Echinacea*, grapes, and/or soy. In some embodiments, the polar emollient is emu oil.

In some embodiments, the polar emollient comprising one or more flavonoid compounds is a natural oil or extract from the genera *Rubus, Ribes, Argania, Nymphaea, Peucedanum* or *Imperatoria, Sambucus, Calendula, Butea*, Citrus (e.g. lime), or species or subspecies thereof In some embodiments, the polar emollient comprising one or more flavonoid compounds comprises Leptospermum Scoparium and/or manuka oil. In some embodiments, the polar emollient comprising one or more flavonoid compounds comprises Argan oil, Sea buckthorn oil, Cicatrol, Protectol, and/or Calendula.

In some embodiments, the emollients comprising one or more flavonoid compounds are present in the formulations of the application in an amount of about 1 wt % to about 20 wt %, about 3 wt % to about 15 wt %, or about 5 wt % to about 12 wt %.

Further Emollients

The polarity of the emollients used in the present can vary depending on the identity of the emulsifiers and emulsion stabilizers, however can nonetheless be selected by a person skilled in the art. In some embodiments, the formulations of the present application comprise both polar emollients and medium polar emollients.

In some embodiments, further polar emollients used in the present application comprise an oil from an animal in the family *Dromaius*, for example Dromiceius (emu) or a plant, such as, Jojoba oil, Olive oil and/or coconut oil.

In some embodiments the one or more further polar emollients are present in an amount of about 1% wt % to about 10 wt %, about 3 wt % to about 7 wt %, or about 4 wt % to about 6 wt %.

In some embodiments, the medium polar emollient is an ester such as octyl palmitate, isopropyl stearate and isopropyl palmitate, or an alcohol such as octyl dodecanol, or mixtures thereof.

In some embodiments the emollients also act as a thickener (stabilizer) and/or a humectant.

In some embodiments, the one or more medium polar emollients are present in an amount of about 1% wt % to about 10 wt %, about 3 wt % to about 7 wt %, or about 4 wt % to about 6 wt %.

Flavonoid-Containing Extract

In some embodiments, the one or more flavonoid-containing extracts for the external phase is any suitable water soluble natural extract comprising a flavonoid with anti-inflammatory and/or antioxidant properties. In some embodiments, the one or more flavonoid-containing extracts are plant-based extracts, including but not limited to, one or more of *Nymphaea caerulea* flower extract, *Peucedanum ostruthium* leaf extract, *Sambuscus nigra* extract, *Calendula* flower Extract, Gingko biloba extract, *Imperatoria Alpallor* extract, *Sambucus Alpallor* extract, Blue lotus extract, *Calendula Alpallor* extract, Masterwort extract, Elderberry extract, Angelica extract, green tea extract, chamomile extract, pomegranate pericarp and *Peucedanum ostruthium* leaf extract.

In some embodiments, the one or more flavonoid-containing extracts for the external phase are present in an amount of about 1% wt % to about 15 wt %, about 3 wt % to about 10 wt %, or about 4 wt % to about 8 wt %.

Penetration Enhancer

The penetration enhancer used in the formulation comprises tetrahydropiperine. It has been found that tetrahydropiperine works in combination with the one or more 1,4-dialdehyde sesquiterpenes to improve penetration of the one or more capsaicinoids in a transdermal base formulation as described herein.

In some embodiments the penetration enhancer further comprises other penetration enhancers known in the art, for example, ethoxydiglycol (transcutanol) and mixtures thereof.

In an embodiment, the penetration enhancer (either tetrahydropiperine or a mixture of tetrahydropiperine and one or more other penetration enhancers) is present in the formulation in an amount of about 0.5 wt % to about 5 wt %, or about 1 wt % to about 2 wt %.

Phospholipid-Complexed Flavonoid

In some embodiments, the flavonoid in the phospholipid-complexed flavonoid is a bioflavonoid isolated from plants such as, but not limited to, *Gingko bilboa, Crataegus* sp., *Passiflora incarnata, Tormentilla potentilla, Tea sinensis., Aurantium* sp., *Citrus* sp., *Eucaliptus* sp., *Matricaria chamomilla, Rheum* sp. and *Fagara sylanthoides*. In some embodiments, the flavonoid is isolated from green tea, buckwheat, the leaves and petioles of asparagus, fruit of the Fava D-Ante tree, fruits and fruit rinds, for example from citrus fruits such as orange, grapefruit, lemon and lime, and berries such as mulberries and cranberries. In some embodiments, the flavonoid is selected from quercetin, myrcetin, apigenin and rutin, and mixtures thereof.

In some embodiments, the phospholipid is any phospholipid, or mixture of phospholipids, from a plant or animal, or any synthetic phospholipid. In some embodiments, the phospholipid is selected from a phosphatidylcholine, a phosphatidylethanolamine, a phosphatidylinostinol, a phosphatidylserine and lecithin, and mixtures thereof In some embodiments, the phospholipid-complexed flavonoid is commercially available. In some embodiments, the phospholipid-complexed flavonoid is prepared by combining the phospholipid and flavonoid in a suitable solvent or mixture of solvents, in a mole ratio of phospholipid:flavonoid of about 0.5 to 2, or about 1, and isolating the resulting complex, for example, but removal of the solvent (s), precipitation and/or lyophilization.

In some embodiments, the phospholipid-complexed flavonoid is present in an amount of about 0.5% wt % to about 5 wt %, about 1 wt % to about 4 wt %, or about 1.5 wt % to about 2.5 wt %.

Complexes of bioflavonoids with phospholipids, their preparation and use, are described, for example in U.S. Pat. No. 5,043,323, the contents of which are incorporated by reference in their entirety.

Water

The balance of the aqueous phase of the composition is made up of water. Further, it is an embodiment that the solvent for the external phase and/or the preservative phase (if present) comprises water. In some embodiments, the water is purified and/or demineralized water. The purified water may, for example, be filtered or sterilized.

In some embodiments, the amount of water in the aqueous phase is about 40 wt % to about 60 wt %, or about 45 wt % to about 55wt % (based on the total weight of the formulation).

In some embodiments, the amount of water in the external phase is about 0.5wt % to about 5 wt %, or about 1 wt % to about 3wt % (based on the total weight of the formulation).

In some embodiments, the amount of water in the preservative phase (if present) is about 0 wt % to about 5 wt %, (based on the total weight of the formulation).

Preservatives

In some embodiments, the formulations of the present application comprise at least one preservative. Preservatives include antimicrobial agents. In some embodiments the preservatives prevent or inhibit the growth of micro-organisms, including bacteria, yeasts and molds. In some embodiments, the preservatives prevent or inhibit undersirable chemical reactions from occurring.

In some embodiments, the preservative comprises a preservative system comprising phenoxyethanol, benzoic acid, and dehydroacetic acid. In some embodiments, the preservative comprises capryl glycol, which also advantageously has humectant and emollient properties. In some embodiments, the preservative comprises chlorphensin. In some embodiments, the preservative comprises ethylhexylglycerin which also advantageously has skin conditioning and emollient properties and acts as a deodorant. In some embodiments, the preservative comprises a natural antimicrobial agent (antibacterial, antifungal, antiviral). In some embodiments, the natural antimicrobial agent is selected from tea tree oil (*Malaleuca alternifolia* leaf oil) and myrtyl lemon essential oil. In some embodiments, the preservative comprises a preservative and a preservative booster.

In some embodiments, other components of the formulation have intrinsic anti-microbial properties.

In some embodiments, the one or more preservatives are present in an amount of about 0% wt % to about 5 wt %, about 1 wt % to about 4 wt %, or about 1.5 wt % to about 3 wt %.

Further Optional Ingredients

In some embodiments, the formulations of the present application further comprise additional ingredients that are common in the transdermal base formulation art. These ingredients are, for example, but not limited to, further active pharmaceutical ingredients, pH adjusters or buffering agents, further solvents, solubilizers, chelating agents, pigments, fragrances, humectants and/or solubilizers.

(a) pH Adjusters/Buffering Agents

In some embodiments, the formulations of the application further comprise one or more pH adjusters, such as acidic, basic, or buffering components. These components may be added to provide the optimal pH balance for the skin. They may also be added to provide an optimal pH for one or more the components of the formulation. In some embodiments the pH of the formulations is adjusted to about 6 to about 7.5.

In some embodiments, the pH adjuster is selected from sodium hydroxide and potassium citrate. In some embodiment, the one or more pH adjusters are present in the formulation in an amount of about 0.05% wt % to about 2.0% wt, about 0.1 wt % to about 1.0 wt %, or about 0.8 wt % to about 0.8 wt %.

In some embodiments, the one or more pH adjusters are in the aqueous phase or the external phase.

(b) Chelating Agents

In some embodiments, the formulations of the application further comprise one or more chelating agents. In some embodiments, the chelating agents bind to metals which can inhibit the activity of the antimicrobial preservatives. In some embodiments, the chelating agent is sodium phytate or ethylendiamine tetraacetic acid (EDTA). In some embodiments, the one or more chelating agents are present in the formulation in an amount of about 0.01% wt % to about 0.2% wt, about 0.02 wt % to about 0.1 wt %, or about 0.03 wt % to about 0.05 wt %.

In some embodiments, the one or more chelating agents are in the aqueous phase or the external phase.

(c) Humectants

In some embodiments, the formulations of the present application further include one or more humectants. In some embodiments, the one or more humectants include, but are not limited to, glycerine (which also acts as an additional solvent).

In some embodiments, the one or more humectants are present in the formulation in an amount of about 0.5 wt % to about 10% wt, about 1 wt % to about 7 wt %, or about 2 wt % to about 5 wt %.

In some embodiments, the one or more humectants are in the aqueous phase.

(d) Solubilizers

In some embodiments, the formulations of the present application further include one or more solubilizers. In some embodiments, the one or more solubilizers include, but are not limited to, inulin lauryl carbonate.

In some embodiments, the one or more solubilizers are present in the formulation in an amount of about 0.01 wt % to about 5% wt, about 0.1 wt % to about 2 wt %, or about 0.2 wt % to about 1 wt %.

In some embodiments, the one or more solubilizers are in the external phase.

(e) Further Active Pharmaceutical Ingredients

In some embodiments, the transdermal formulation of the present application further comprise other active pharmacological ingredients (APIs). As used herein, API may include active molecules derived from natural, synthetic or semi-synthetic means, as well as other active ingredients.

In some embodiments, the further active pharmaceutical ingredient (API) is solubilised or dispersed in an effective amount of a suitable vehicle (e.g. solvent(s) or diluent(s)). A skilled person can readily determine which solvents or diluents will be appropriate for a particular API. In some embodiments, the API is included in the external phase. In some embodiments, the further API is included in an amount of about 0.01 wt % to about 1 wt %, about 0.05 wt % to about 0.5 wt %, or about 0.075 wt %.

In some embodiments, the transdermal formulation comprises:
(a) an aqueous phase comprising water and at least one emulsion stabilizer (such as xanthan gum);
(b) an oil phase comprising at least one emulsifier (such as cetearyl olivate, sorbitan olivate), at least one emulsion stabilizer (such as beeswax), at least one emollient comprising at least one flavonoid (such as natural oil or extract of *Ribes Nigrum* (Black Currant) Seed Oil and/or *Rubus Idaeus* (Raspberry) Seed Oil), and at least one other emollient (such as isopropyl palmitate);
wherein the oil and aqueous phase form an emulsion;
(c) an external phase comprising at least one flavonoid containing-extract (such as *Peucedanum ostruthium* leaf extract or *Calendula Officinalis* Flower Extract), at least one penetration enhancer comprising tetrahyropiperine, at least one capsaicinoind, polygodial or TMP and at least one phospholipid-complexed flavonoid (such as lecithin and rutin); and optionally
(d) at least one preservative phase (such as benzoic acid and caprylyl glycol).

In some embodiments, the formulations of the present application are prepared using a procees that comprises:
a) heating an aqueous phase comprising water and at least one emulsion stabilizer to a first temperature;
(b) heating an oil phase comprising at least one emulsifier, at least one emulsion stabilizer, at least one emollient comprising at least one flavonoid, and at least one other emollient to the first temperature;
(c) adding the aqueous phase to the oil phase with stirring at the first temperature and continuing to stir at the first temperature until an emulsion is formed;
(d) cooling the emulsion in (c) to a second temperature; and, in any order:
(e) adding one or more external phases comprising at least one flavonoid containing-extract, at least one penetration enhancer, at least one phospholipid-complexed flavonoid, at least one 1,4-dialdehyde sesquiterpene and at least one capsaicinoid to the emulsion at the second temperature; and optionally
(f) adding one or more preservative phases to the emulsion.

In some embodiments, the first temperature is about 65° C. to about 85° C., about 70° C. to about 80° C., or about 75° C.

In some embodiments, the second temperature is about 30° C. to about 50° C., about 35° C. to about 45° C., or about 40° C.

In some embodiments, the process further comprises preparing the external phase wherein the at least one phospholipid-complexed flavonoid is stirred with water for a sufficient amount of time to become hydrated prior to being combined with the remaining ingredients for the external phase.

In some embodiments, the phases and emulsions are mixed with an homogenizer prior to combining with other phases.

II. Methods of the Application

In some embodiments, the present application includes a method for the transdermal administration of one or more capsaicinoids comprising administering an effecting amount of one or more of the formulations of the present application to a subject in need thereof, wherein the one or more formulations comprise the one or more capsaicinoids. In further embodiments, the present application includes a use of one or more formulations of the present application for the administration of one or more capsaicinoids to a subject, wherein the one or more formulations comprise the one or more capsaicinoids.

The present application includes therapeutic methods and uses of the formulations described herein. In some embodiments, the formulations are used in methods to treat one or more capsaicinoid-responsive conditions. In some embodiments, the formulations are used in methods for treating or providing relief from minor aches and pains of muscles and joints associated with arthritis, backache, strains and sprains. In some embodiments, the formulations are used in methods for treating or reducing the symptoms of peripheral neuropathy, such as post-herpetic neuraglia caused by shingles.

Accordingly, the present application includes methods for treating one or more capsaicinoid-responsive conditions, comprising administering an effective amount of a transdermal formulation of the application to a subject in need thereof. Also included is a use of a transdermal formulation of the application to treat one or more capsaicinoid-responsive conditions. In some embodiments the capsaicinoid-responsive conditions are selected from pain (including painful neuropathies and musculosketal pain), inflammation, itch, psoriasis, pruritis and microbial infections. In some embodiments, the formulations of the application are used in conjuction with other therapies to treat the diseases, conditions or disorders.

In some embodiments, the formulations of the present application advantageously provide treatment with a lower amount of irritation or burning sensation compared to other transdermal or topical capsaicinoid formulations. This allows the formulations of the application to be applied to sensitive areas, such as around diabetic and open wounds, around the eyes and/or around the genital area.

Using the methods and formulations disclosed herein, therapeutically effective amounts of capsaicinoid compounds can be administered (e.g., transdermally or topically) to a subject much more rapidly than is possible using conventional formulations. Capsaicinoid-mediated therapeutic benefits (including reduction of the density of cutaneous or mucosal nociceptors and amelioration of capsaicin-responsive conditions and/or their characteristic symptoms) can be achieved by administration of the capsaicinoid at, for example without irritation, at a lower concentration (due to enhanced permeation) and/or for a shorter period than heretofore believed or demonstrated. For some applications it will be desirable to use a relatively high concentration, while in other cases there will be advantages to using a lower concentration.

EXAMPLES

The following non-limiting examples are illustrative of the present application:

Example 1

A Transdermal Base Formulation containing Polygodial Source/Capsaicin Source and Penetration Enhancer A therapeutic formulation comprising the ingredients and their respective amounts listed in Table 1 was prepared as follows:

Step A: Demineralized water, chelating agent, humectant and thickener were combined in a master kettle and heated to 75° C. The solution mixture was stirred until homogenous.

Step B: In another kettle, ingredients of phase A were combined and heated to 75° C. Once a homogenous solution was achieved, the solution mixture was added into the master kettle, followed by rapid stirring until complete emulsification, about 2-3 minutes.

Step C: The solution mixture in the master kettle was gradually cooled, while stirring. When the reaction temperature reached 35-40° C., ingredients of phase C were added one by one, whereby with each addition the solution was mixed until homogenous. The phospholipid complexed rutin was mixed with demineralized water until homogeneous prior to adding to the master kettle.

Step D: In a separate vessel, the ingredients of Phase D were added and mixed. Once a homogenous solution was achieved, the solution mixture was added into the master kettle, followed by stirring until the solution became homogenous.

Step E: Allow the formulation to cool to room temperature.

Step F: The viscosity using a Brookfield RVT, T4, 2 RPM instrument and pH measurements of the final solution were taken. The viscosity and pH values should be within the range of 85,000-200,000 cps and 6.0-7.5 at 25° C., respectively.

Figure 1:
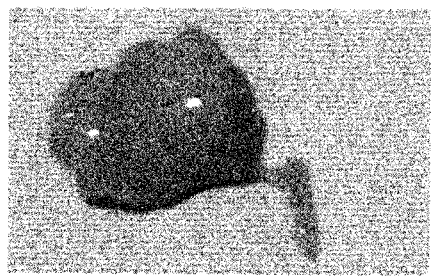
Figure 1:
Figure 1:
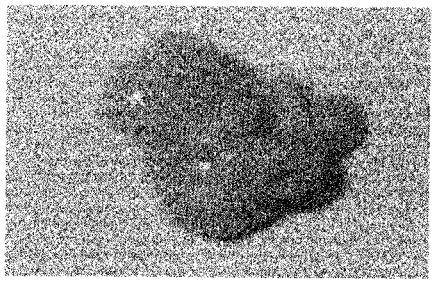
Figure 1:
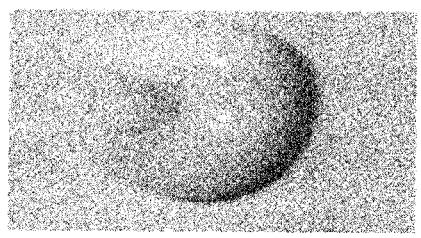

A picture of the formulations is shown in FIG. 1 where it is clearly seen that the formulations of the application, (b) and (d), have a lighter, more desirable color (due to potential staining) compared with prior formulations comprising capsaicin (a) or rutin (c).

Example 2

Preparation of Exemplary Transdermal Base Formulation

A transdermal base formulation comprising the ingredients and their respective amounts listed in Table 2 was prepared as follows:

Step A: Demineralized water and chelating agent were added to a master kettle and heated to 75° C. The solution mixture was stirred until homogenous to ensure that the chelating agent was completely hydrated.

Step B: In a separate vessel, humectant and thickener were mixed until homogenous and added to the master kettle in Step A.

Step C: In another kettle, ingredients of phase A were combined and heated to 75° C. Once a homogenous solution was achieved, the solution mixture was added into the master kettle, followed by rapid stirring until complete emulsification, about 2-3 minutes.

Step D: The solution mixture in the master kettle was gradually cooled, while stirring. When the reaction temperature reached 35-40° C., ingredients of phase C were added one by one, whereby with each addition the solution was mixed until homogenous.

Step E: In a separate vessel, the ingredients of Phase D were added and mixed. Once a homogenous solution was achieved, the solution mixture was added into the master kettle, followed by stirring until the solution became homogenous.

Step F: In a separate vessel, the ingredients of Phase F were combined until homogeneous. The resulting solution was added into the master kettle.

Step G: In a separate vessel, phospholipid complexed flavonoid was mixed with demineralized water. The homogenous solution was then added to the master kettle and further cooled to room temperature.

Step I: The viscosity using a Brookfield RVT, T4, 2 RPM instrument and pH measurements of the final solution were taken. The viscosity and pH values should be within the range of 85,000-200,000 cps and 6.0-7.5 at 25° C., respectively.

Example 3

(A) The Effect of Penetration Enhancers on the Flux Rates of Osthole and Capsaicin using the PAMPA Assay
I. Material and Methods
A. Preparation of Standards:

1 mg/mL stock solutions of polygodial, tetrahydropiperine (Cosmoperine™), osthole, dimethylisosorbide (DMI), Tazmanian Mountain Pepper (TMP), capsaicin and warfarin were prepared in methanol and stored at −20 ° C.

Prisma buffer preparation: Added 1.25 mL of Prisma™ HT buffer to 48.75 mL distilled water. Adjusted to pH 7.0 by adding 0.5 M NaOH dropwise.

50 µg/mL solutions of capsaicin, warfarin and osthole were prepared by adding 50 µL of the 1 mg/mL solutions to 950 µL of MeOH:$H_2O$ (50:50).

Donor Well Solutions: Experiment 1—Polygodial, Osthole and Capsaicin with DMI and THP Preparation of Capsaicin Solutions:

5 µg/mL solution of capsaicin was prepared in Prisma™ buffer solution by adding 5 µL of 1 mg/mL solution of capsaicin to 0.995 mL Prisma™ buffer.

5 µg/mL of capsaicin+5 µg/mL solution of DMI was prepared in Prisma™ buffer solution by adding 5 µL of 1 mg/mL of DMI and 5 µL of 1 mg/mL of capsaicin solution to 0.990 mL Prisma™ buffer.

5 µg/mL of capsaicin+5 µg/mL solution of THP was prepared in Prisma™ buffer solution by adding 5 µL of 1 mg/mL of THP and 5 µL of 1 mg/mL of capsaicin solution to 0.990 mL Prisma™ buffer.

Preparation of Osthole Solutions:

5 µg/mL solution of osthole was prepared in Prisma™ buffer solution by adding 5 µL of 1 mg/mL solution of osthole to 0.995 mL Prisma™ buffer.

5 µg/mL of osthole+5 µg/mL solution of DMI was prepared in Prisma™ buffer solution by adding 5 µL of 1 mg/mL of DMI and 5 µL of 1 mg/mL of osthole solution to 0.990 mL Prisma™ buffer.

5 µg/mL of osthole+5 µg/mL solution of THP was prepared in Prisma™ buffer solution by adding 5 µL of 1 mg/mL of THP and 5 µL of 1 mg/mL of osthole solution to 0.990 mL Prisma™ buffer.

Donor Well Solutions: Experiment 2—Osthole and Capsaicin with Polygodial, TMP and THP Preparation of Capsaicin Solutions:

5 µg/mL solution of capsaicin was prepared in Prisma™ buffer solution by adding 5 µL of 1 mg/mL solution of capsaicin to 0.995 mL Prisma™ buffer. (Solution A)

5 µg/mL of capsaicin+5 µg/mL solution of polygodial was prepared in Prisma™ buffer solution by adding 5 µL of 1 mg/mL of polygodial and 5 µL of 1 mg/mL of capsaicin solution to 0.990 mL Prisma™ buffer. (Solution B)

5 µg/mL of capsaicin+5 µg/mL solution of TMP was prepared in Prisma™ buffer solution by adding 5 µL of 1 mg/mL of TMP and 5 µL of 1 mg/mL of capsaicin solution to 0.990 mL Prisma™ buffer. (Solution C)

5 µg/mL of capsaicin+5 µg/mL TMP+5 µg/mL solution of tetrahydropiperine was prepared in Prisma™ buffer solution by adding 5 µL of 1 mg/mL of TMP and 5 µL of 1 mg/mL tetrahydropiperine and 5 µL of 1 mg/mL of capsaicin solution to 0.985 mL Prisma™ buffer. (Solution D)

5 µg/mL of capsaicin+5 µg/mL solution of tetrahydropiperine was prepared in Prisma™ buffer solution by adding 5 µL of 1 mg/mL of tetrahydropiperine and 5 µL of 1 mg/mL of capsaicin solution to 0.990 mL Prisma™ buffer. (Solution E)

Preparation of Osthole Solutions:

5 µg/mL solution of osthole was prepared in Prisma™ buffer solution by adding 5 µL of 1 mg/mL solution of osthole to 0.995 mL Prisma™ buffer. (Solution F)

5 µg/mL of osthole+5 µg/mL solution of polygodial was prepared in Prisma™ buffer solution by adding 5 µL of 1 mg/mL of polygodial and 5 µL of 1 mg/mL of osthole solution to 0.990 mL Prisma™ buffer. (Solution G)

5 µg/mL of osthole+5 µg/mL solution of TMP was prepared in Prisma™ buffer solution by adding 5 µL of 1 mg/mL of TMP and 5 µL of 1 mg/mL of osthole solution to 0.990 mL Prisma™ buffer. (Solution H)

5 µg/mL of osthole+5 µg/mL TMP+5 µg/mL solution of tetrahydropiperine was prepared in Prisma™ buffer solution by adding 5 µL of 1 mg/mL of TMP and 5 µL of 1 mg/mL tetrahydropiperine and 5 µL of 1 mg/mL of osthole solution to 0.985 mL Prisma™ buffer. (Solution I)

5 µg/mL of osthole+5 µg/mL solution of tetrahydropiperine was prepared in Prisma™ buffer solution by adding 5 µL of 1 mg/mL of tetrahydropiperine and 5 µL of 1 mg/mL of osthole solution to 0.990 mL Prisma™ buffer. (Solution J)

Standard Series:

Solution J: A solution of 1 µg/mL osthole and 1 µg/mL capsaicin and 125 ng/mL warfarin was prepared by adding 40 µL of 50 µg/mL solution of osthole, 40 µL of 50 µg/mL solution of capsaicin and 5 µL of 50 µg/mL solution of warfarin to 1.915 mL of MeOH, 0.1% AcOH.

Solution K: A solution of 125 ng/mL of warfarin was prepared by adding 5 µL of 50 µg/mL solution of warfarin to 1.995 mL of MeOH, 0.1% AcOH.

The standard series was prepared by serial diluting solution J with solution K to give concentrations of 1000.0 ng/mL, 500.0 ng/mL, 250.0 ng/mL, 125.0 ng/mL, 62.5 ng/mL, 31.3 ng/mL, 15.6 ng/mL, 7.8 ng/mL, 3.9 ng/mL of osthole and capsaicin and a constant concentration of 125 ng/mL warfarin. The serial dilutions were quantified using the ratio of the peak area of capsaicin and osthole to the peak area of warfarin as the assay parameter. Peak area ratios were plotted against osthole and capsaicin concentrations and standard curves in the form of y=A+Bx were calculated using weighted least squares linear regression.

Figure 2:
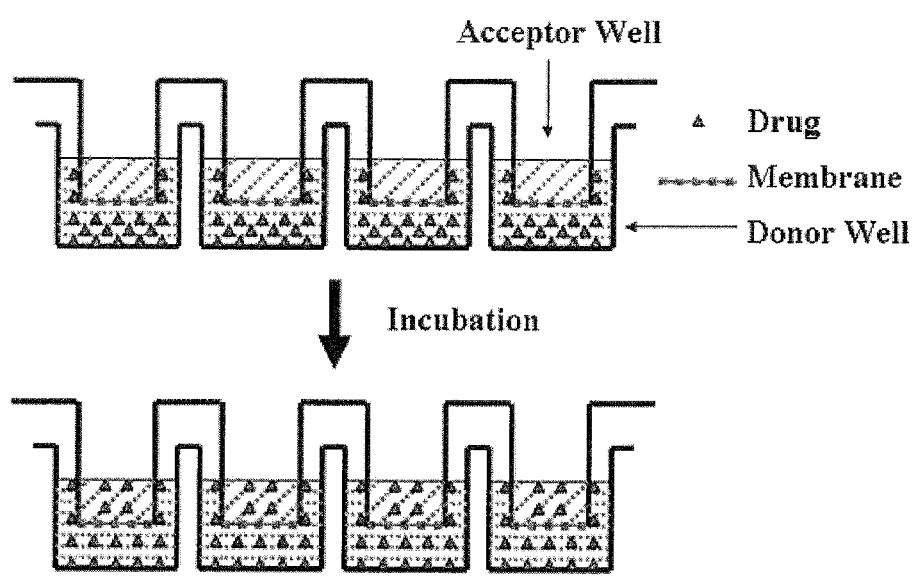
FIG. 2 is a schematic showing the general format and apparatus for the PAMPA assay.

B. PAMPA Assay:

A schematic graphically depicting the PAMPA apparatus is shown in FIG. 2.

Removed PAMPA hydration solution from the fridge and allowed to come to room temperature. Added 3.7 mL to each trough in the reservoir corresponding to each set of 8 PAMPA wells that were to be used. Assembled the PAMPA plate onto the reservoir plate and sealed using parafilm. Allowed plate to hydrate overnight.

Added 200 µL of each prepared donor solution (above) to the PAMPA donor plate well in duplicate. Removed the PAMPA plate from the reservoir plate and placed on the donor plate. Added 200 µL of the prisma buffer to each acceptor well and cover. Collect 5 µL from each well at time points 0.5 h, 1 h, 1.5 h, 2 h, 2.5 h, and 5 h and add to 95 µL of a 131 µg/mL solution of warfarin (prepared by adding 5.2 µL of 50 µg/mL warfarin stock solution to 1.9948 mL of MeOH, 0.1% AcOH) in a HPLC vial with insert.

(B) Comparison of 8 Exemplary Cream Formulations Measuring the Permeation of Capsaicin and Osthole using the PAMPA in vitro System
Preparation of Standards:

1 mg/mL stock solutions of capsaicin, osthole and warfarin were prepared in methanol and stored at −20° C.

Prisma™ buffer preparation: Added 1.25 mL of Prisma™ buffer to 48.75 mL distilled water. Adjust to pH 7.0 by adding 0.5 M NaOH dropwise.

50 µg/mL solutions of capsaicin, osthole and warfarin were prepared by adding 50 µL of the 1 mg/mL solutions to 950 µL of MeOH.

Standard Series:

Solution A: A solution of 1 µg/mL osthole and 1 µg/mL capsaicin and 125 ng/mL warfarin was prepared by adding 40 µL of 50 µg/mL solution of capsaicin and 40 µL of 50 µg/mL solution of osthole and 5 µL of 50 µg/mL solution of warfarin to 1.915 mL of MeOH (0.1%).

Solution B: A solution of 125 ng/mL of warfarin was prepared by adding 5 µL of 50 µg/mL solution of warfarin to 1.995 mL of MeOH (0.1% AcOH)

The standard series was prepared by serial diluting solution A with solution B to give concentrations of 1000.0 ng/mL, 500.0 ng/mL, 250.0 ng/mL, 125.0 ng/mL, 62.5 ng/mL, 31.3 ng/mL, 15.6 ng/mL, 7.8 ng/mL, 3.9 ng/mL of capsaicin and osthole and a constant concentration of 125 ng/mL warfarin. The serial dilutions were quantified using the ratio of the peak area of capsaicin to the peak area of warfarin as the assay parameter. Peak area ratios were plotted against capsaicin concentrations and standard curves in the form of y=A+Bx were calculated using weighted least squares linear regression.
PAMPA Assay:

Removed PAMPA hydration solution from the fridge and allowed to come to room temperature. Added 3.7 mL to each trough in the reservoir corresponding to each set of 8 PAMPA wells that are to be used. Assembled the PAMPA plate onto the reservoir plate and sealed using parafilm. Allowed plate to hydrate overnight.

~200 µL of each cream to be tested were added by 1 mL syringe equipped with a needle to the PAMPA donor plate well in triplicate. The PAMPA plate acceptor well plate was removed from the reservoir plate and placed on the donor plate. 200 µL of the Prisma™ buffer was added to each acceptor well and the cover was put in place. 10 µL from each acceptor well was removed by pipette at predetermined time points and add to 30 µL of a 166 µg/mL solution of warfarin (prepared by adding 6.6 µL of 50 µg/mL solution of warfarin solution to 1.9933 mL of MeOH 0.1% AcOH) in a HPLC vial with insert. This was injected directly into the LCMS and analyzed using the protocol below.
Extraction and Quantification of Capsaicin in the Cream:

Solution C—A solution of 138 ng/mL of warfarin was prepared by adding 5.5 µL of the 50 µg/mL solution of warfarin to 1.9945 mL methanol (0.1% AcOH).

Solution D—A solution of 138 ng/mL of capsaicin+138 ng/mL warfarin was prepared by adding 5.5 µL of the 50 µg/mL solution of warfarin and 5.5 µL of the 50 µg/mL solution of capsaicin 1.989 mL methanol (0.1% AcOH).

Solution E—A solution of 138 ng/mL of osthole+138 ng/mL warfarin was prepared by adding 5.5 µL of the 50 µg/mL solution of warfarin and 5.5 µL of the 50 µg/mL solution of osthole 1.989 mL methanol (0.1% AcOH).
Doped Samples—Capsaicin:

Weighed an amount of exemplary base cream (between 5 and 10 mgs) into scintillation vial and recorded weight. Added 1% of weight of the 50 µg/mL solution of capsaicin to vial (for example if 7.5 mgs of cream, then added 75 µL of stock solution). Added 99% of weight of 50:50 MeOH:H₂O to vial (for example if 7.5 mgs then added 7.425 mL) to give a total of 1 mg/mL solution. Sonicated 30 mins. Transfered 1 mL of extract to 1.7 mL polypropylene microtubes (MCT-175-C; Catalog no.311-04-051, Axygen), and centrifuged 3 minutes at 11000 rpm. Transfered 10 µL of extract to 90 µL solution C in HPLC vials (Agilent, product number 5182-0716) with inserts (product number 5181-1270, Agilent) and mixed. Injected 10 µL to LCMS.
Doped Samples—Osthole:

Weighed an amount of exemplary base cream (between 5 and 10 mgs) into scintillation vial and recorded weight. Added 1% of weight of 50 µg/mL solution of osthole to vial (for example if 7.5 mgs of cream, then added 75 µL of stock solution). Added 99% of weight of 50:50 MeOH:H₂O to vial (for example if 7.5 mgs then added 7.425 mL) to give a total of 1 mg/mL solution. Sonicated 30 mins. Transferred 1 mL of extract to 1.7 mL polypropylene microtubes (MCT-175-C; Catalog no.311-04-051, Axygen), and centrifuged 3 minutes at 11000 rpm. Transferred 10 µL of extract to 90 µL solution C in HPLC vials (Agilent, product number 5182-0716) with inserts (product number 5181-1270, agilent) and mix. Inject 10 µL to LCMS.
Spike Samples:

Weighed an amount of exemplary base cream (between 5 and 10 mgs) into scintillation vial and recorded weight. Added enough 50:50 MeOH:H₂O to vial (example if 7.5 mgs then added 7.5 mL) to give a total of 1 mg/mL solution. Sonicated 30 mins. Transferred 1 mL of extract to 1.7 mL polypropylene microtubes (MCT-175-C; Catalog no.311-04-051, Axygen), and centrifuged 3 minutes @ 11000 rpm. Transferred 10 µL of extract to 90 µL solution D (spiked capsaicin) or solution E (spiked osthole) in HPLC vials (Agilent, product number 5182-0716) with inserts (product number 5181-1270, Agilent) and mixed. Injected 10 µL to LCMS.
Blank Samples:

Weighed an amount of exemplary cream (between 5 and 10 mgs) into scintillation vial and recorded weight. Added enough 50:50 MeOH:H₂O to vial (for example if 7.5 mgs then added 7.5 mL) to give a total of 1 mg/mL solution. Sonicated 30 mins. Transferred 1 mL of extract to 1.7 mL polypropylene microtubes (MCT-175-C; Catalog no.311-04-051, Axygen), and centrifuged 3 minutes @ 11000 rpm. Transferred 10 µL of extract to 90 µL solution C in HPLC vials (Agilent, product number 5182-0716) with inserts (product number 5181-1270, Agilent) and mixed. Injected 10 µL to LCMS.
Unknown Samples:

Weighed an amount of cream to be analyzed (between 5 and 10 mgs) into scintillation vial and recorded weight. Added enough 50:50 MeOH:H₂O to vial (for example if 7.5 mgs then added 7.5 mL) to give a total of 1 mg/mL solution. Sonicated 30 mins. Transferred 1 mL of extract to 1.7 mL polypropylene microtubes (MCT-175-C; Catalog no.311-04-051, Axygen), and centrifuged 3 minutes @ 11000 rpm. Transferred 10 µL of extract to 90 µL solution C in HPLC vials (Agilent, product number 5182-0716) with inserts (product number 5181-1270, Agilent) and mixed. Injected 10 µL to LCMS.

II. Results and discussion

Several over-the-counter (OTC) products are available that contain capsaicin as an active ingredient for the treatment of, for example, nerve pain, diabetic nerve pain and shingles pain. Another putative bioactive is osthole, a component of the *angelica archangelic* extract included within another OTC product for treatment of nerve pain. TMP is a commercial extract from the Tazmanian pepper fruit. One of the primary bioactives of this extract is hypothesized to be a polygodial, a 1,4-dialdehyde sesquiterpene. The present study investigated the effect of known penetration enhancers on the flux rate velocity of actives from these products in a parallel artificial membrane permeability assay (PAMPA). PAMPA is an assay in which a compound diffuses through a lipid bilayer matrix supported by a porous artificial membrane from a donor well to an acceptor well.

Piperine is a natural product alkaloid isolated from black pepper and long pepper. The related tetrahydropiperine is also naturally occurring but of much lower abundance and is known to increase the bioavailability of some nutrients, drugs and other bioactives. (U.S. Pat. No. # 6,849,645). Under the tradename Cosmoperine®, tetrahydropiperine (THP) is a branded ingredient that can be used in cosmetic formulations to enhance the uptake and bioavailability of transdermally applied active compounds. In contrast to the enchancers previously mentioned, Dimethyl Isosorbide (DMI) is a synthetic solvent used as an ingredient in personal health care products useful for several purposes, one being for transdermal delivery enhancement of active molecules.

The effectiveness of the pure compounds THP and DMI to effect capsaicin and osthole penetration was assessed using the PAMPA system.

The experiment was conducted in two parts with the first round of testing (Experiment #1) focused on the comparison of the natural penetration enhancer tetrahydropiperine and the synthetic solvent DMI. The subsequent experimental design (Experiment #2) focused on the comparison of the natural penetration enhancer THP in the presence of polygodial and/or TMP. For all experiments, the PAMPA (FIG. 2) was constructed as described and the concentrations of capsaicin or osthole were quantified at 0, 0.5, 1.0, 1.5, 2.0, 2.5, and 5 hours for the bioactive alone or in the presence of an equimolar concentration of enhancer.

Figure 3:
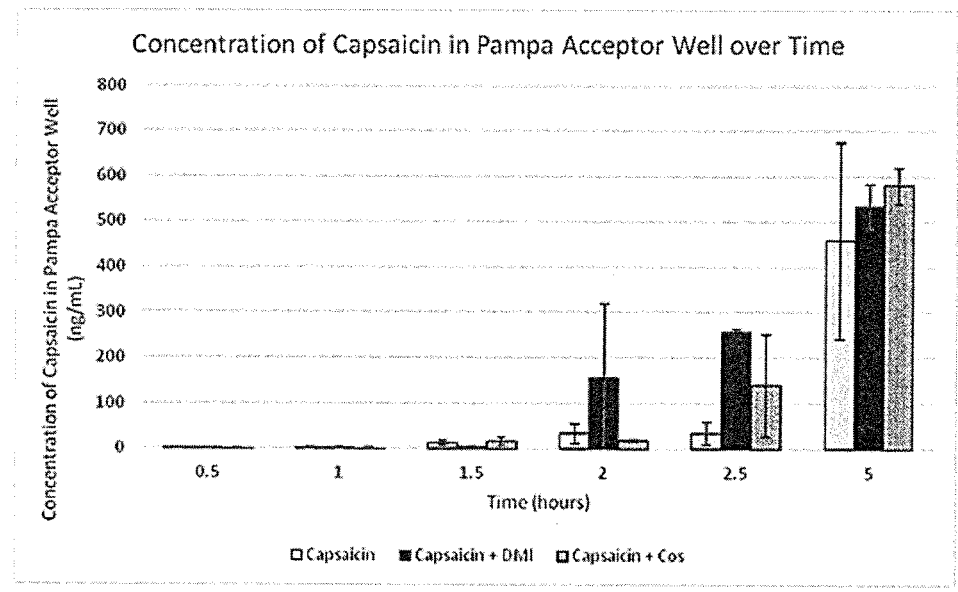
FIG. 3 is a bar graph showing the effect of natural and synthetic penetration enhancers on the permeation of capsaicin in the PAMPA system. Capsaicin concentration was quantified in the acceptor well at various timepoints after loading the donor compartment with capsaicin alone (5

Experiment 1—Capsaicin: When comparing THP, DMI, or capsaicin alone over the five hour period, neither penetration enhancer demonstrated a statistically significant increase in capsaicin flux in the PAMPA system (FIG. 3).

Experiment 1—Osthole: When comparing THP, DMI, or osthole alone over the five hour period there was a statistically significant increase in the presence of THP at 2.0 and 2.5 hours (FIG. 4). This penetration enhancement effect of THP did not extend to the five hour timepoint. No observable enhancement was attributed to DMI, although the results for this enhancer included much larger variance (S.E.M.) compared to the tandem THP analysis (FIG. 4).

Experiment 2—Capsaicin: This experiment focused on a series of natural penetration enhancers in the context of capsaicin flux in the PAMPA system in the presence or absence of polygodial and/or TMP. When comparing polygodial, TMP, THP, a combination of THP and TMP, or capsaicin alone over the five hour period there was no statistically significant increase in capsaicin under the conditions tested within the experiment (FIG. 5). Counter intuitively, polygodial, TMP, and the combination of TMP with THP appear to decreased the flux rate of capsaicin (FIG. 5). There is a statistically significant decrease in the concentration of capsaicin in the acceptor well for TMP and TMP+THP compared to the control (FIG. 5).

Experiment 2—Osthole: This experiment focused on a series of natural penetration enhancers in the context of osthole flux in the PAMPA system in the presence or absence of polygodial and/or TMP. When comparing polygodial, TMP, THP, a combination of THP and TMP, or osthole alone over the five hour period there was a statistically significant increase in penetration osthole in the presence of THP over the control at 2.0 hours (FIG. 6). This penetration enhancement effect of THP did not extend to subsequent timepoints. In contrast, TMP decreased the flux rate of osthole at 5 hours (FIG. 6).

Using the PAMPA system to compare various hypothetical penetration enhancers on the flux rate of osthole demonstrated a statistically significant increase for tetrahydropiperine (THP), however the observed increase in penetration was a transient event. No effect was observed for DMI, whereas polygodial and TMP may in fact suppress the membrane penetration by osthole. Indeed, the transient enhancement demonstrated by THP for both capsaicin and osthole was neutralized when another additive (TMP) was included in a combinatorial experiment.

These results demonstrate that certain penetration enhancers behave in a transient mechanism in this in vitro assay and that some putative enhancers in fact suppress penetration across the membrane.

Given the observed variation between penetration enhancers and the counter-intuitive suppressive results observed for some additives, the flux rates of these compounds was studied within the context of a complex mixture, such as an exemplary transdermal base.

The effectiveness of the exemplary transdermal base formulations that include THP, TMP, or both were assessed for their ability to augment the flux rate of the bioactives capsaicin and osthole using the PAMPA system.

The various formulations were loaded into the PAMPA donor well (~200 µL) in triplicate and the acceptor well was sampled at 0.5, 1.0, 1.5, 2.0, 2.5, 5.0, 10.0, and 24 hours. However, the levels of capsaicin did not enter the range of quantification until 5.0 hours (data not shown).

Capsaicin: The effects of enhancers on capsaicin penetration in exemplary base formulations using the PAMPA system indicated a statistically significant difference at 24 hours, between the control (capsaicin alone) and the THP+TMP formulation where neither additive increased the flux rate of capsaicin when tested individually (FIG. 7).

This experiment was repeated two additional times and the same trend for enhanced penetration was observed for the THP+TMP formula, however in these repeat experiments the trend was not statistically (Pvalue >0.05) significant (FIG. 8). Greater than triplicate sets of data may be needed as some experimental standard deviations vary widely from experiment to experiment (see e.g FIGS. 3 and 4). For example, the control wells at 24 hours demonstrate similar averages (70 ng/mL and 59.1 ng/mL) with distinct deviations (+/−2.8 ng/mL and +/−18.4 ng/mL, respectively).

Osthole: The effects of enhancers on osthole penetration in exemplary base formulations did not demonstrate any significant effect.

Overal eight exemplary base cream formulations were evaluated for their effectiveness to increase the permeation of actives through the PAMPA membrane, 4 for capsaicin, and 2 for osthole.

With respect to capsaicin, neither THP nor the TMP by themselves increased penetrance however, a combinatorial formulation of the two did generate a significant increase with repeat experiments recapitulating this trend (FIG. 7). It is theorized that a formulation of 2.0% (w/w) TMP and 0.1% (w/w) THP is beneficial for capsaicin bioavailability in the exemplary base.

With respect to osthole no observed penetration enhancement was measured for formulations that included TMP or the combination of THP with TMP. Furthermore, the flux rate for these formulations was not different from the commercial LivRelief—Nerve Pain product (data not shown).

Example 4

Effectiveness of Exemplary Formulations of the Application for Treating Pain due to Swelling and Inflammation An exemplary formulation of the application, such as the formulation of Example 1, was provided to 11 patients under a physician's care for pain and inflammation due to osteoarthritis and/or rheumatoid arthritis, and/or pain due to swelling from trauma or mobility issues. The patients were blind as to the contents of the formulation. Of the 11 patients, 7 have responded that the exemplary formulation showed efficacy in reducing their pain and inflammation. The remaining 4 patients provided no response. No patients reported any burning sensation with use of the formulation.

Example 5

Effectiveness of Exemplary Formulations of the Application for Treating Pain due to Swelling and Inflammation An exemplary formulation of the application, such as the formulation of Example 1, was provided to 26 patients under a physician's care for nerve pain (e.g. peripheral neuropathy or diabetic neuropathy) as manifested by burning, pins and needles, electric shock and/or noise chattering. The patients were blind as to the contents of the formulation. Of the 26 patients, 12 have responded that the exemplary formulation showed efficacy in reducing their nerve pain, 1 reported that the formulation was not effective and the remaining 13 patients provided no response. No patients reported any burning sensation with use of the formulation.

Example 6

Primary Cutaneous Tolerance on Healthy Volunteers by Single 48-hr Patch Test Primary Cutaneous Tolerance Test of an Exemplary Cream Formulation of the Applicant Test Product: Exemplary formulation of the application, for example as described in Example 1, (Lot no. 15-260-083).

Control: pure Vaseline USP

Application: The test product was used without dilution and was generously applied on the entire surface of the patch. The total area of the application is about 2.25 cm$^2$.

Material: The patches used in this study were TruMed® semi-occlusive, cotton "BBA149-129 Absorbent" with "3M 1530 Tape" adhesive backing.

Type of study: Monocentric and open-ended, meaning the evaluator, volunteers, and sponsors alike, were aware of the nature of the test material however not the contents.

Volunteers: A total of 25 volunteers were recruited based on the inclusion and exclusion criteria.

Subject Demographics:

| Sex | Number | Age | Average Age |
|---|---|---|---|
| Male | 6 | 19 to 67 | 50.33 |
| Female | 19 | 22 to 70 | 50.11 |
| Total | 25 | 19 to 70 | 50.16 |

Inclusion Criteria:
1. Volunteers of the feminine or masculine sex, aged 18 years or older,
2. With phototype I to IV according to Fitzpatrick's classification (very clear to mat) and with a skin type that does not interfere with the assessment of cutaneous reactions,
3. Healthy and without any dermal anomalies on the areas to be tested,
4. With no excessive body hair, especially on the test area,
5. Who will cooperate and be present for a follow-up at every visit, informed and sensitized about the duration and importance of controls allowing for a complete compliance with the study protocol,
6. Who have read, signed and dated the Informed Consent Forms upon full knowledge of the risks involved with the study,
7. Women who use a method of contraception (oral contraceptive, condoms, spermicidal creams, an intra-uterine device (IUS), abstinence . . . ).

Exclusion Criteria:
1. Volunteers with a history of skin irritation or allergies to the type of product to be tested or in general, with allergies to certain foods, to certain chemical products, to jewellery . . . ,
2. With a serious illness, health problem or chronic or progressive disease (asthma, diabetes, cancer, immunological deficiency, ablated organ . . . ),
3. With a history of eczema, dermatitis, psoriasis or significant dermal anomalies on the test area,
4. On medication or having taken medication in the last 7 days prior to the study that could affect skin characteristics or could bias the study (antibiotics, anti-inflammatory drugs, steroids, antihistamines . . . ),
5. Who frequently use tanning salons or foresee exposure to the sun,
6. Who abuse alcohol, drugs and/or tobacco,
7. Women who are pregnant, breastfeeding or expecting to become pregnant during the study.

Design of the study:

Procedure: Prior to application of the patches, the test area (upper back, between the two shoulder blades) was carefully examined and wiped with alcohol if necessary (oily skin only). A patch containing the test product and another containing the negative control were applied to the test area, and were left in contact with the skin for 48 hours. Care was taken when positioning the patches to minimize the possibility of displacement or rubbing. The volunteers were not to remove or wet the patches and were to keep them covered with clothing and to avoid exposure to sun or other sources of tanning. The uses of any other topical pharmaceutical or cosmetic products were not permitted during the study.

Observation and data collection: Forty-eight (48) hours after application, the patches were removed and all observations (types described below) were recorded. In addition to the observations made and recorded by Evalulab, the volunteers were encouraged to observe and report Evalulab any immediate or delayed reactions such as redness, irritation, itching, or other sensations on the application sites for up to 72 hours after application. The test area and its surrounding area were observed for erythema, oedema, vesicles, blisters, ulcerations, dryness and acne (papules). These parameters were evaluated and graded as follows:

Reaction Scale:
0=No visible reaction,
S=Dryness,
+=Erythema barely noticeable,

1=Mild/slight erythema in the patch zone,
2=Moderate but well defined erythema and presence of slight or barely visible oedema,
3=Marked erythema, presence of oedema and vesicles,
4=Severe erythema, presence of vesicles, blisters, and ulcerations.

All observations and comments provided by the volunteers were recorded in their respective Case Report Form. The obtained scores were then entered in a tabular form showing the number of reactions after treatment (Table 3).

Example 7

Primary Cutaneous Tolerance on Healthy Volunteers by Single 48-hr Patch Test

Primary Cutaneous Tolerance Test

Test Product: A second exemplary formulation of the application, for example as described in Example 1 (Lot no. 15-202-063).

Control: pure Vaseline USP

Application: The product was used without dilution and was generously applied on the entire surface of the patch. The total area of the application is about 2.25 cm$^2$.

Material: The patches used in this study were TruMed® semi-occlusive, cotton "BBA149-129 Absorbent" with "3M 1530 Tape" adhesive backing.

Type of study: Monocentric and open-ended, meaning the evaluator, volunteers, and sponsors alike, were aware of the nature of the test material.

Volunteers: A total of 25 volunteers were recruited based on the inclusion and exclusion criteria.

Subject Demographics:

| Sex | Number | Age | Average Age |
| --- | --- | --- | --- |
| Male | 6 | 19 to 67 | 50.33 |
| Female | 19 | 22 to 70 | 50.11 |
| Total | 25 | 19 to 70 | 50.16 |

Inclusion Criteria:
1. Volunteers of the feminine or masculine sex, aged 18 years or older,
2. With phototype I to IV according to Fitzpatrick's classifincation (very clear to mat) and with a skin type that does not interfere with the assessment of cutaneous reactions,
3. Healthy and without any dermal anomalies on the areas to be tested,
4. With no excessive body hair, especially on the test area,
5. Who will cooperate and be present for a follow-up at every visit, informed and sensitized about the duration and importance of controls allowing for a complete compliance with the study protocol,
6. Who have read, signed and dated the Informed Consent Forms upon full knowledge of the risks involved with the study,
7. Women who use a method of contraception (oral contraceptive, condoms, spermicidal creams, an intra-uterine device (IUS), abstinence . . . ).

Exclusion Criteria:
1. Volunteers with a history of skin irritation or allergies to the type of product to be tested or in general, with allergies to certain foods, to certain chemical products, to jewellery . . . ,
2. With a serious illness, health problem or chronic or progressive disease (asthma, diabetes, cancer, immunological deficiency, ablated organ . . . ),
3. With a history of eczema, dermatitis, psoriasis or significant dermal anomalies on the test area,
4. On medication or having taken medication in the last 7 days prior to the study that could affect skin characteristics or could bias the study (antibiotics, anti-inflammatory drugs, steroids, antihistamines . . . ),
5. Who frequently use tanning salons or foresee exposure to the sun,
6. Who abuse alcohol, drugs and/or tobacco,
7. Women who are pregnant, breastfeeding or expecting to become pregnant during the study.

Design of the study:

Procedure: Prior to application of the patches, the test area (upper back, between the two shoulder blades) was carefully examined and wiped with alcohol if necessary (oily skin only). A patch containing the test product and another containing the negative control were applied to the test area, and were left in contact with the skin for 48 hours. Care was taken when positioning the patches to minimize the possibility of displacement or rubbing. The volunteers were not to remove or wet the patches and were to keep them covered with clothing and to avoid exposure to sun or other sources of tanning. The uses of any other topical pharmaceutical or cosmetic products were not permitted during the study.

Observation and data collection: Forty-eight (48) hours after application, the patches were removed and all observations (types described below) were recorded. In addition to the observations made and recorded by Evalulab, the volunteers were encouraged to observe and report Evalulab any immediate or delayed reactions such as redness, irritation, itching, or other sensations on the application sites for up to 72 hours after application. The test area and its surrounding area were observed for erythema, oedema, vesicles, blisters, ulcerations, dryness and acne (papules). These parameters were evaluated and graded as follows:

Reaction Scale:
0=No visible reaction,
S=Dryness,
+=Erythema barely noticeable,
1=Mild/slight erythema in the patch zone,
2=Moderate but well defined erythema and presence of slight or barely visible oedema,
3=Marked erythema, presence of oedema and vesicles,
4=Severe erythema, presence of vesicles, blisters, and ulcerations.

All observations and comments provided by the volunteers were recorded in their respective Case Report Form. The obtained scores were then entered in a tabular form showing the number of reactions after treatment (Table 4).

Results and Discussion for Examples 6 and 7

Primary cutaneous tolerance tests on healthy volunteers were undertaken to determine the primary cutaneous tolerance on human skin for the exemplary formulations of the application as well as determine the existence of an allergic pre-disposition with a single 48 hour patch application.

Twenty-five volunteers, men and women from 19 to 70 years of age (average age=50.16), were recruited and completed this study. No pertinent reaction to the test products was observed during the study (Tables 3 and 4). Additionally, no reactions were observed with the controls (Vaseline USP) for both treatment studies.

Therefore, under the conditions of these studies, and based on the results obtained, the compositions of the application produced no signs of cutaneous irritation and were therefore considered as non-irritant.

Example 8

Determination of the Photo-Toxicity Potential of a Topical Product Photo-Toxicity Study Test Product: Exemplary formulation of the application, for example as described in Example 1 (Lot no. 15-260-083).

Control: pure Vaseline USP

Material: A Multiport, 150 W, Model 601 UV simulator, equipped with Xenon Arc lamp (Solar Light Company, Philadelphia, Pa.) was used. In accordance with the FDA requirements, the simulator was equipped with UG-11 filter and a UV cut off filter (UVB or UVA), producing a spectrum of UV rays (290-400 nm) similar to natural sunlight impacting the surface of the earth, with an aperture of >1 cm$^2$. The intensity, time, and therefore the total dose of UV exposure was measured and controlled by a dosimeter, Model PMA 2100.

Type of study: Monocentric and open-label study, meaning the evaluator, volunteers, and sponsors alike, were aware of the nature of the test material.

Volunteers: A total of 10 volunteers were recruited based on the inclusion and exclusion criteria.

Volunteer Demographics:

| Sex | Number | Age | Average Age |
|---|---|---|---|
| Male | 2 | 51 to 55 | 53 |
| Female | 8 | 22 to 64 | 45.4 |
| Total | 10 | 22 to 64 | 46.9 |

Inclusion Criteria:
1. Male or female volunteers, aged 18 years or older,
2. With phototype I, II or III based on the Fitzpatrick classification,
3. Without excessive hair on the test area,
4. Healthy and without any dermal anomalies on the areas to be tested that may interfere with the results of the study,
5. Cooperating in the study, able to be monitored at each visit, aware of the demands and duration of the controls, thus allowing perfect adherence to the established protocol,
6. Who have read, signed and dated the Informed Consent Forms upon full knowledge of the risks involved in the study,
7. Women who use a method of contraception (oral contraceptive, condoms, spermicidal creams, an intra-uterine device (IUS), abstinence . . . ).

Exclusion Criteria:
1. Volunteers with a history of skin irritation or allergies to the type of product to be tested or in general, with allergies to certain foods, to certain chemical products, to jewellery . . . ,
2. With a history of photo dermatitis, psoriasis or other cutaneous anomalies on the tested zones,
3. Who suffer from a serious illness or health problem or a critical or progressive disease (asthma, diabetes, cancer, immunological deficiency, removed organ . . . ),
4. Who have taken prescription or over the counter medication (at a frequency equal to or more than 3 doses per week) that could affect skin characteristics or could bias the study (antibiotics, steroids, antihistamines, anti-inflammatories . . . ) within 7 days of study start,
5. Who abuse alcohol, drugs and/or tobacco,
6. Women who are pregnant, breastfeeding or expecting to become pregnant during the study.

Design study:

Application of the test product and control (Vaseline USP) 24 hours before UVA irradiation: Prior to applying each product, the skin of the volunteer's back was carefully examined and wiped with alcohol. Twenty milligrams (20 mg) of test product were placed into two Finn® Chambers, and then applied to the back of the volunteer. The Vaseline control was applied in the same manner using two Finn® Chambers. The first Finn® Chamber site for each product will be the irradiated test site, and the second Finn® Chamber site will be used as a control and will not receive any radiation. The products were left in contact with the skin for 24 hours before irradiation. Volunteers were instructed to avoid wetting the Finn® Chambers or exposing themselves to sunlight or other tanning sources. They were to keep the Finn® Chambers covered with clothing. The use of topical pharmaceutical products or other skin care products on the test area was not permitted during the study. Ingestion of medication or any treatment that could alter the results of the study was also prohibited.

UVA Irradiation: 24 hours after product application, a first Finn® Chamber was removed from one of the test sites, and the excess of product was wiped clean. The test site was then irradiated with a 10 Joules/cm$^2$ dose of UVA radiation using the Solar Simulator. After irradiation, the second Finn® Chamber was removed as well as the excess of product. This site was not irradiated and served as a control test site. The same procedure was performed with control (Vaseline) sites. Volunteers had to avoid wetting the test sites or exposing themselves to sunlight or other tanning sources. They were to keep their back covered with clothing.

Evaluation: All cutaneous responses such as erythema/redness, browning, oedema, were observed and recorded immediately after irradiation, 1 hour and 24 hours after irradiation. Readings were also taken at 48 hours if necessary. According to the reaction pattern, it may be possible to distinguish between phototoxic and photoallergic mechanisms.

Observations and data collection:

The irradiated test sites and non-irradiated test sites were observed for erythema, oedema, vesicles, blisters, papules, ulcerations, dryness and browning. These parameters were evaluated and graded as follows:

Reaction Scale:
0=No visible reaction,
+=Barely noticeable reaction,
1=Mild/slight erythema or browning in the patch zone,
2=Moderate but well defined erythema or browning and presence of slight or barely visible oedema,
3=Marked erythema or browning and possibility of oedema,
4=Severe erythema or browning, possibility of oedema, vesicles, blisters and/or ulcerations.

Observed Parameters:
Erythema: E
Browning: Br
Oedema: OE
Vesicle: V
Blister: B
Dryness: S
Papule: P
Ulceration: U In addition to the observations made and recorded by Evalulab, the volunteers were encouraged to observe and report to Evalulab any immediate or delayed reactions such as redness, irritation, itching or other sensations on the test sites for up to 48 hours after application. All observations and comments reported by the volunteers were recorded in their respective Case Report Forms. The obtained scored were then entered in a tabular form showing the number of reactions after treatment (Table 5).

Example 9

Determination of the Photo-toxicity Potential of a Topical Product

Photo-Toxicity Study

Test Product: A second exemplary formulation of the application, for example as described in Example 1 (Lot no. 15-202-063).

Control: pure Vaseline USP

Material: A Multiport, 150 W, Model 601 UV simulator, equipped with Xenon Arc lamp (Solar Light Company, Philadelphia, Pa.) was used. In accordance with the FDA requirements, the simulator was equipped with UG-11 filter and a UV cut off filter (UVB or UVA), producing a spectrum of UV rays (290-400 nm) similar to natural sunlight impacting the surface of the earth, with an aperture of >1 $cm^2$. The intensity, time, and therefore the total dose of UV exposure was measured and controlled by a dosimeter, Model PMA 2100.

Type of study: Monocentric and open-label study, meaning the evaluator, volunteers, and sponsors alike, were aware of the nature of the test material.

Volunteers: A total of 10 volunteers were recruited based on the inclusion and exclusion criteria.

Volunteer Demographics:

| Sex | Number | Age | Average Age |
| --- | --- | --- | --- |
| Male | 2 | 51 to 55 | 53 |
| Female | 8 | 22 to 64 | 45.4 |
| Total | 10 | 22 to 64 | 46.9 |

Inclusion Criteria:
1. Male or female volunteers, aged 18 years or older,
2. With phototype I, II or III based on the Fitzpatrick classification,
3. Without excessive hair on the test area,
4. Healthy and without any dermal anomalies on the areas to be tested that may interfere with the results of the study,
5. Cooperating in the study, able to be monitored at each visit, aware of the demands and duration of the controls, thus allowing perfect adherence to the established protocol,
6. Who have read, signed and dated the Informed Consent Forms upon full knowledge of the risks involved in the study,
7. Women who use a method of contraception (oral contraceptive, condoms, spermicidal creams, an intra-uterine device (IUS), abstinence . . . ).

Exclusion Criteria:
1. Volunteers with a history of skin irritation or allergies to the type of product to be tested or in general, with allergies to certain foods, to certain chemical products, to jewellry . . . ,
2. With a history of photo dermatitis, psoriasis or other cutaneous anomalies on the tested zones,
3. Who suffer from a serious illness or health problem or a critical or progressive disease (asthma, diabetes, cancer, immunological deficiency, removed organ . . . ),
4. Who have taken prescription or over the counter medication (at a frequency equal to or more than 3 doses per week) that could affect skin characteristics or could bias the study (antibiotics, steroids, antihistamines, anti-inflammatories . . . ) within 7 days of study start,
5. Who abuse alcohol, drugs and/or tobacco,
6. Women who are pregnant, breastfeeding or expecting to become pregnant during the study.

Design study:

Application of the test product and control (Vaseline USP) 24 hours before UVA irradiation: Prior to applying each product, the skin of the volunteer's back was carefully examined and wiped with alcohol. Twenty milligrams (20 mg) of test product were placed into two Finn® Chambers, and then applied to the back of the volunteer. The Vaseline control was applied in the same manner using two Finn® Chambers. The first Finn® Chamber site for each product will be the irradiated test site, and the second Finn® Chamber site will be used as a control and will not receive any radiation. The products were left in contact with the skin for 24 hours before irradiation. Volunteers were instructed to avoid wetting the Finn® Chambers or exposing themselves to sunlight or other tanning sources. They were to keep the Finn® Chambers covered with clothing. The use of topical pharmaceutical products or other skin care products on the test area was not permitted during the study. Ingestion of medication or any treatment that could alter the results of the study was also prohibited.

UVA Irradiation: 24 hours after product application, a first Finn® Chamber was removed from one of the test sites, and the excess of product was wiped clean. The test site was then irradiated with a 10 Joules/$cm^2$ dose of UVA radiation using the Solar Simulator. After irradiation, the second Finn® Chamber was removed as well as the excess of product. This site was not irradiated and served as a control test site. The same procedure was performed with control (Vaseline) sites. Volunteers had to avoid wetting the test sites or exposing themselves to sunlight or other tanning sources. They were to keep their back covered with clothing.

Evaluation: All cutaneous responses such as erythema/redness, browning, oedema, were observed and recorded immediately after irradiation, 1 hour and 24 hours after irradiation. Readings were also taken at 48 hours if necessary. According to the reaction pattern, it may be possible to distinguish between phototoxic and photoallergic mechanisms.

Observations and data collection:

The irradiated test sites and non-irradiated test sites were observed for erythema, oedema, vesicles, blisters, papules, ulcerations, dryness and browning. These parameters were evaluated and graded as follows:

Reaction Scale:
0=No visible reaction,
+=Barely noticeable reaction,
1=Mild/slight erythema or browning in the patch zone,
2=Moderate but well defined erythema or browning and presence of slight or barely visible oedema,
3=Marked erythema or browning and possibility of oedema,
4=Severe erythema or browning, possibility of oedema, vesicles, blisters and/or ulcerations.

Observed Parameters:
Erythema: E
Browning: Br
Oedema: OE
Vesicle: V
Blister: B
Dryness: S
Papule: P
Ulceration: U In addition to the observations made and recorded by Evalulab, the volunteers were encouraged to observe and report to Evalulab any immediate or delayed reactions such as redness, irritation, itching or other sensations on the test sites for up to 48 hours after application. All observations and comments reported by the volunteers were recorded in their respective Case Report Forms. The obtained scored were then entered in a tabular form showing the number of reactions after treatment (Table 6).

Results and Discussion for Examples 8 and 9

Studies evaluating the photo-toxicity potential of the test products on the skin of healthy volunteers were conducted.

Ten volunteers, men and women, from 22 to 64 years of age (average age=46.9), were included in these studies. All volunteers were able to complete the studies without incidence.

The data obtained during the study for the test product "Lot No. 15-260-083" and control (Vaseline USP) are presented in Table 5. With the exception of a few reactions after UVA irradiation graded E+or Br+(i.e., barely noticeable erythema or browning), no pertinent reactions were observed for the test product or control.

Under the conditions of the study, the test product "Lot No. 15-260-083" did not produce any pertinent photo-toxic reactions immediately or 24 hours after UVA exposure in the test panel.

On the other hand, a significant number of immediate and delayed reactions (i.e., graded E+, Br+and El to E4) were observed in the test panel after UVA irradiation with the test product "Lot No. 15-202-063" (Table 6). No pertinent reactions were observed for the control (Vaseline). A significant number of photo-toxic reactions immediately after, 24 hours and 48 hours after UVA exposure were observed for the majority of the panel. Therefore, the test product "Lot No. 15-202-063" may be considered as photo-toxic and possible photo-allergenic and patients using this cream should be advised to avoid exposure to UVA light. While not wishing to be limited by theory, it is assumed that the phytotoxicity of the product is due to the presence of furanocoumarins in one of the extracts in the product.

Example 10

Material Purification and Quantification

Polygodial, Osthole, THP, Capsaicin and Warfarin Isocratic chromatographic separation was performed on a C18 column (Zorbax eclipse XDB C18 column (4.6×150 mm, 5 micron particle size Agilent USKH009316) with guard using a mobile phase of MeOH (0.1% acetic acid): water (0.1% acetic acid) (97:3) at a flow rate of 0.5 mL/min for 6 min. The first two minutes was sent to the waste and the compounds all elute between 4-5.5 min. There was no post time.The column temperature was 30° C. and the autosampler temperature was maintained at 4° C. The sample injection volume was 10 µL. A 4000 Q trap from AB Sciex Instruments equipped with an electrospray ionization (ESI) was used in the positive ion mode with multiple reaction monitoring (MRM) for the quantitative analysis. Nitrogen was used as the collision gas and the curtain gas. The curtain gas was 10.00 psi, the collision gas was 6, the ion spray voltage was 4500 volts, the temperature was 350° C., and gas sources 1 and 2 were −14 psi. The declustering potential was 40 volts, the exit potential was 10.00 volts, the focusing lens 1 was −10.50 volts and the cell exit potential was 4.00 volts. Quantification was performed using the transitions m/z 235.3→83 (CE=30 v, 20 msec) for polygodial, m/z 245.1→189.1 (CE=15V, 20 msec) for osthole, m/z 290.1→205.1 (CE=30V, 20 msec) for THP, m/z 306→137 (CE=30 V, 100 msec) for capsaicin, and m/z 309.3→163 (CE=30 V, 20 msec) for warfarin. Analytical data were acquired and quantification processing was performed by using Analyst software.

Table 7 reports the amount of capsaicin that was found in various test formulations (comparative and exemplary). This confirms the presence of capsaicin in the exemplary formulations. Table 8 reports the amount of osthole that was found in the various test formulations.

Example 11

Effectiveness of Exemplary Formulations of the Application for Treating Joint Pain Study Design: The study was performed at 2 different data collection sites with a total number of 28 patients (N=12 and 16 respectively) suffering from various joint paint. The study consisted assessing pain levels in patients using the self-reported Brief Pain Inventory Questionnaire at different time-points after administration of an exemplary formulation prepared according to the application (Example 1): visit 2 or baseline, visit 3 and visit 4 with a week difference between each visit.

Efficacy

Outcome measures were taken from the Brief pain inventory questionnaire. Results are illustrated in Figrues 9 and 10 (Black bars represent data collected from both sites (N=28); Grey bars represent data collected from one site (N=16)(* p=0.04)). Question #3 (left 3 bars "BPI_Visit#_3" in FIG. 9) of the Brief Pain Inventory assessed the rating of worst pain in the last 24H. Question 5 (right 3 bars of FIG. 9) of the BPI was to assess rating of average pain. As shown in FIG. 9, there was a significant lowering of the pain experienced by the patients between baseline (V2), visit 3 (V3) and visit 4 (V4) as measured by the rating of the worst pain in the past 24 hours. FIG. 10 shows lowering of pain experienced by the patients between baseline (V2) and visit 4 (V4). No patients reported any burning sensation with use of the formulation.

Prophetic Example 12

PAMPA Assay Assessment of Capsaicincoid in Exemplary Base Formulation

Study Design: The PAMPA assay is used to compare the rate of penetration of capsaicincoid in creams. A transdermal base formulation containing a capsaicincoid source is prepared according to Example 1 above. Another formulation is prepared for comparison in which the capsaicincoid source is added in the oil phase. The PAMPA assay is used to assess the rate of penetration of the capsaicincoid in the formulations through a lipid bilayer matrix.

Methods

PAMPA Assay:

The PAMPA hydration solution (Pion, 120706) is removed from the refrigerator and allowed to come to room temperature for 1 hour. 3.7 mL of the hydration solution is added to each trough in the reservoir plate corresponding to each set of 8 pampa wells to be hydrated. The pampa precoated sandwich (Pion, 120657) is then assembled with the hydration reservoir on the bottom, the pampa plate in the middle and cover on top. The plate is wrapped in parafilm and allowed to hydrate overnight without being moved or disturbed.

A solution of pampa assay buffer is prepared by adding 1.25 mL of Prisma HT buffer (Pion 110151) to 48.75 mL of distilled water. The pH of the buffer is adjusted to 7.0 with 0.5 M NaOH.

Creams to be tested are first transferred into a 10 mL syringe. As much of the air as possible is pushed from the syringe with the plunger. A second 10 mL syringe is attached to the first syringe via connector. The cream is forced from one syringe to the other until one large bubble containing most of the air is adjacent to the plunger of one of the syringes. Then the cream is pushed into the other syringe leaving the bubble of air in the other syringe. The cream containing syringe is then detached from the 10 mL syringe and attached to a 1 mL syringe. The cream is carefully transferred to the 1 mL syringe until full (overflowing with plunger removed). The plunger is then replaced. A 14 gauge needle is then attached to the end of the syringe, and the plunger is pushed until the cream filled the dead volume of the needle. The plunger is pushed until it reached an even graduation (ex. 1.0 mL). The needle is placed just touching the middle of the bottom of the pampa donor well, and very slowly and carefully not to introduce air pockets, 0.2 mL of the cream is added to the donor well. This is repeated until the wells contained the appropriate amount of creams to be tested. The pampa sandwich is then assembled and then 200 µL of prisma buffer is added to each receiver well using a multichannel pipette. 5 µL of the receiver solution is sampled at 1 h, 2 h, 3 h, 4 h and 5 h time points. The 5 µL sampled is added to 95 µL of 50:50 MeOH:H$_2$O in a 96 well plate and stirred by pipette in preparation for injection to the LCMS for analysis.

Standard Series:

A series of capsaicinoid standards are prepared. For example, capsaicinoids are weighed into a scintillation vial (5-10 mg) and enough MeOH:H$_2$O (50:50) is added to make a 500 µg/mL solution. The solution is sonicated to aid dissolution. A 50 µg/mL solution of capsaicinoid is prepared by adding 100 µL of the 500 µg/mL solution to 900 µL of MeOH:H$_2$O (50:50) which is then vortexed for 10 seconds. A 1 µg/mL solution of capsaicinoid is made by adding 20 µL of 50 µg/mL solution to 980 µL of MeOH:H$_2$O. The 1 µg/mL solution of capsaicinoid is serial diluted (100 µL) with 50:50 MeOH:H$_2$O in the wells of a 96 well plate to give a standard series with capsaicinoid concentrations of 3.9, 7.8, 15.6, 31.2, 62.5, 15, 250, 500, and 1000 ng/mL.

HPLC- MS Instrumentation and Conditions:

Isocratic chromatographic separation is performed on a C18 column (Agilent eclipse XDB C18 column (4.6×150 mm, 5 micron particle size, Agilent USKH095544) with guard using a mobile phase of MeOH (4 mM NH$_4$OAc):H$_2$O (4 mM NH$_4$OAc) (80:20) at a flow rate of 0.50 mL/min for 5 min. The first two minutes is sent to the waste and the capsaicinoid elutes. The column temperature is 40 °C and the autosampler temperature is maintained at 4° C. The sample injection volume is 10 µL and the injector is set to 0 mm with bottom sensing enabled. A Linear Ion Trap 5500 Quadropole from AB Sciex Instruments equipped with an electrospray ionization (ESI) is used in the negative ion mode with multiple reaction monitoring (MRM) for the quantitative analysis. Nitrogen is used as the collision gas and the curtain gas. The curtain gas is 15.00 psi, the collision gas is medium, the ion spray voltage is −4500 volts, the temperature is 550° C., and gas sources 1 and 2 are 20 and 20 psi respectively. The declustering potential is −150 volts, the exit potential is −10.00 volts and the cell exit potential is −15.00 volts. Analytical data is acquired and quantification processing is performed by using Analyst software.

Results and Discussion

The increase in the rate of penetration of the formulation with capsaicincoid present in the external phase is observed to be higher across the PAMPA membrane compared to the formulation with capsaicincoid present in the oil phase.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Transdermal Cream Formulation

| | Ingredients | % |
|---|---|---|
| Phase A (Oil Phase) | Emulsifiers | 7-8% |
| | Wax Stabilizer | 2-3% |
| | Polar Emollient Oils | 5-12% |
| | Medium Polar Emollient | 4-5% |
| Phase B (Water Phase) | Water | 50-55% |
| | Humectant | 2-4% |
| | Thickener | 0.0-0.8% |
| | Chelating Agent | 0.01-1% |
| Phase C (Active Phase) | Flavonoid Containing Extracts | 6-8% |
| | Phospholipid-complexed Flavonoid | 2% |
| | Water | 2% |
| | Penetration Enhancer | 1-2% |
| | 1,4-dialdehyde sesquiterpene source | 2-4% |
| | Capsaicinoid source | 0.01-0.1% |
| Phase D (Preservative Phase) | Preservative | 1-2% |

TABLE 2

| | Ingredients | % |
|---|---|---|
| Phase A | Emulsifiers | 7% |
| | Wax Stabilizer | 2.5% |
| | Polar Emollient Oils | 11.5% |
| | Medium Polar Emollient | 4.5% |
| Phase B | Water | 53.55% |
| | Humectant | 3% |
| | Thickener | 0.4% |
| | Chelating Agent | 0.05% |
| Phase C | Flavonoid Containing Extracts | 7% |

TABLE 2-continued

| | Ingredients | % |
|---|---|---|
| Phase D | Preservative | 1.1% |
| | Solubilizer | 0.5% |
| | Penetration Enhancer | 1.5% |
| Phase E | Phospholipid-complexed Flavonoid | 2% |
| | Water | 2% |
| Phase F | Buffering Agents | 1% |
| | Water soluble preservative booster | 0.8% |
| | Water | 1.6% |
| | Total | 100.00% |

TABLE 3

Individual results of 48-Hour Patch-Test from Example 6

| Volunteer Identification | | | | Observations | |
|---|---|---|---|---|---|
| No. | | Initials | Sex | 48 h | 72 h |
| 01 | -0413- 001 | MC | F | 0 | 0 |
| 01 | -0413- 002 | ML | F | 0 | 0 |
| 02 | -0413- 003 | PC | M | 0 | 0 |
| 01 | -0413- 004 | CR | F | 0 | 0 |
| 01 | -0413- 005 | CP | F | 0 | 0 |
| 01 | -0413- 006 | NK | F | 0 | 0 |
| 02 | -0413- 007 | AA | M | 0 | 0 |
| 02 | -0413- 008 | BB | M | 0 | 0 |
| 01 | -0413- 009 | IL | F | 0 | 0 |
| 01 | -0413- 010 | VP | F | 0 | 0 |
| 01 | -0413- 011 | NC | F | 0 | 0 |
| 01 | -0413- 012 | JB | F | 0 | 0 |
| 02 | -0413- 013 | SC | M | 0 | 0 |
| 01 | -0413- 014 | ML | F | 0 | 0 |
| 02 | -0413- 015 | PL | M | 0 | 0 |
| 01 | -0413- 016 | ME | F | 0 | 0 |
| 01 | -0413- 017 | AC | F | 0 | 0 |
| 01 | -0413- 018 | DR | F | 0 | 0 |
| 01 | -0413- 019 | EJ | F | 0 | 0 |
| 01 | -0413- 020 | EM | F | 0 | 0 |
| 01 | -0413- 021 | TM | F | 0 | 0 |
| 01 | -0413- 022 | CL | F | 0 | 0 |
| 01 | -0413- 023 | SB | F | 0 | 0 |
| 02 | -0413- 024 | GS | M | 0 | 0 |
| 01 | -0413- 025 | EF | F | 0 | 0 |

TABLE 4

Individual results of 48-Hour Patch-Test from Example 7

| Volunteer Identification | | | | Observations | |
|---|---|---|---|---|---|
| No. | | Initials | Sex | 48 h | 72 h |
| 01 | -0413- 001 | MC | F | 0 | 0 |
| 01 | -0413- 002 | ML | F | 0 | 0 |
| 02 | -0413- 003 | PC | M | 0 | 0 |
| 01 | -0413- 004 | CR | F | 0 | 0 |
| 01 | -0413- 005 | CP | F | 0 | 0 |
| 01 | -0413- 006 | NK | F | 0 | 0 |
| 02 | -0413- 007 | AA | M | 0 | 0 |
| 02 | -0413- 008 | BB | M | 0 | 0 |
| 01 | -0413- 009 | IL | F | 0 | 0 |
| 01 | -0413- 010 | VP | F | 0 | 0 |
| 01 | -0413- 011 | NC | F | 0 | 0 |
| 01 | -0413- 012 | JB | F | 0 | 0 |
| 02 | -0413- 013 | SC | M | 0 | 0 |
| 01 | -0413- 014 | ML | F | 0 | 0 |
| 02 | -0413- 015 | PL | M | 0 | 0 |
| 01 | -0413- 016 | ME | F | 0 | 0 |
| 01 | -0413- 017 | AC | F | 0 | 0 |
| 01 | -0413- 018 | DR | F | 0 | 0 |
| 01 | -0413- 019 | EJ | F | 0 | 0 |
| 01 | -0413- 020 | EM | F | 0 | 0 |
| 01 | -0413- 021 | TM | F | 0 | 0 |
| 01 | -0413- 022 | CL | F | 0 | 0 |
| 01 | -0413- 023 | SB | F | 0 | 0 |
| 02 | -0413- 024 | GS | M | 0 | 0 |
| 01 | -0413- 025 | EF | F | 0 | 0 |

TABLE 5

Individual photo-toxicity results for (A) the test product and (B) the control (Vaseline) for Example 8

| # Vol | Immediate reaction after irradiation | | D0 + 1 H | | D0 + 24 H | | D0 + 48 H | |
|---|---|---|---|---|---|---|---|---|
| | Irradiated test Zone | Non Irradiated test Zone | Irradiated test Zone | Non Irradiated test Zone | Irradiated test Zone | Non Irradiated test Zone | Irradiated test Zone | Non Irradiated test Zone |
| (A) | | | | | | | | |
| 001 | 0 | 0 | 0 | 0 | 0 | 0 | 0 | 0 |
| 002 | 0 | 0 | 0 | 0 | 0 | 0 | 0 | 0 |
| 003 | 0 | 0 | 0 | 0 | 0 | 0 | 0 | 0 |
| 004 | E+ | 0 | 0 | 0 | 0 | 0 | 0 | 0 |
| 005 | 0 | 0 | 0 | 0 | 0 | 0 | 0 | 0 |
| 006 | 0 | 0 | 0 | 0 | 0 | 0 | 0 | 0 |
| 007 | Br+ | 0 | 0 | 0 | 0 | 0 | 0 | 0 |
| 008 | Br+ | 0 | 0 | 0 | 0 | 0 | 0 | 0 |
| 009 | 0 | 0 | 0 | 0 | E+ | 0* | 0 | 0 |
| 010 | Br+ | 0 | E+ | 0 | 0 | 0 | 0 | 0 |
| (B) | | | | | | | | |
| 001 | 0 | 0 | 0 | 0 | 0 | 0 | 0 | 0 |
| 002 | 0 | 0 | 0 | 0 | 0 | 0 | 0 | 0 |
| 003 | 0 | 0 | 0 | 0 | 0 | 0 | 0 | 0 |
| 004 | 0 | 0 | 0 | 0 | 0 | 0 | 0 | 0 |

TABLE 5-continued

Individual photo-toxicity results for (A) the test product and (B) the control (Vaseline) for Example 8

| # Vol | Immediate reaction after irradiation | | D0 + 1 H | | D0 + 24 H | | D0 + 48 H | |
|---|---|---|---|---|---|---|---|---|
| | Irradiated test Zone | Non Irradiated test Zone | Irradiated test Zone | Non Irradiated test Zone | Irradiated test Zone | Non Irradiated test Zone | Irradiated test Zone | Non Irradiated test Zone |
| 005 | 0 | 0 | 0 | 0 | 0 | 0 | 0 | 0 |
| 006 | 0 | 0 | 0 | 0 | 0 | 0 | 0 | 0 |
| 007 | 0 | 0 | 0 | 0 | 0 | 0 | 0 | 0 |
| 008 | 0 | 0 | 0 | 0 | 0 | 0 | 0 | 0 |
| 009 | 0 | 0 | 0 | 0 | 0 | 0 | 0 | 0 |
| 010 | 0 | 0 | 0 | 0 | 0 | 0 | 0 | 0 |

*A reaction graded E+ was observed 24 hours after irradiation on the non-irradiated test site of volunteer #009. A re-challenge test was performed on this volunteer. No reaction was observed.

TABLE 6

Individual photo-toxicity results for (A) the test product and (B) the control (Vaseline) for Example 9

| # Vol | Immediate reaction after irradiation | | D0 + 1 H | | D0 + 24 H | | D0 + 48 H | |
|---|---|---|---|---|---|---|---|---|
| | Irradiated test Zone | Non Irradiated test Zone | Irradiated test Zone | Non Irradiated test Zone | Irradiated test Zone | Non Irradiated test Zone | Irradiated test Zone | Non Irradiated test Zone |
| (A) | | | | | | | | |
| 001 | 0 | 0 | 0 | 0 | E3 | 0 | E4 | 0 |
| 002 | 0 | 0 | 0 | 0 | E+ | 0 | E3 | 0 |
| 003 | 0 | 0 | 0 | 0 | 0 | 0 | 0 | 0 |
| 004 | E+ | 0 | 0 | 0 | E+ | 0 | 0 | 0 |
| 005 | 0 | 0 | 0 | 0 | E2 | 0 | E2 | 0 |
| 006 | 0 | 0 | 0 | 0 | E1 | 0 | 0 | 0 |
| 007 | Br+ | 0 | 0 | 0 | E2 | 0 | E4 | 0 |
| 008 | Br+ | 0 | 0 | 0 | E+ | 0 | 0 | 0 |
| 009 | 0 | 0 | 0 | 0 | E1 | 0 | E+ | 0 |
| 010 | Br+ | 0 | E+ | 0 | E1 | 0 | E3 | 0 |
| (B) | | | | | | | | |
| 001 | 0 | 0 | 0 | 0 | 0 | 0 | 0 | 0 |
| 002 | 0 | 0 | 0 | 0 | 0 | 0 | 0 | 0 |
| 003 | 0 | 0 | 0 | 0 | 0 | 0 | 0 | 0 |
| 004 | 0 | 0 | 0 | 0 | 0 | 0 | 0 | 0 |
| 005 | 0 | 0 | 0 | 0 | 0 | 0 | 0 | 0 |
| 006 | 0 | 0 | 0 | 0 | 0 | 0 | 0 | 0 |
| 007 | 0 | 0 | 0 | 0 | 0 | 0 | 0 | 0 |
| 008 | 0 | 0 | 0 | 0 | 0 | 0 | 0 | 0 |
| 009 | 0 | 0 | 0 | 0 | 0 | 0 | 0 | 0 |
| 010 | 0 | 0 | 0 | 0 | 0 | 0 | 0 | 0 |

TABLE 7

Quantification of Capsaicin in Creams

| Formulation | Lot Number | % (w/w) Capsaicin |
|---|---|---|
| Control | 15-261-083 | 0.0010 |
| TMP | (15-111-035 | 0.0010 |
| TMP + THP | 15-260-083 | 0.0010 |
| THP | 15-292-092 | 0.0011 |
| Base Cream, negative control | 13261-4 | 0.0000 |

TABLE 8

Quantification of Osthole in Creams

| Formulation | Lot Number | % (w/w) Osthole |
|---|---|---|
| COS + TMP | 15-202-063 | 0.060 |
| TMP | 15-149-042 | 0.071 |
| LivRelief - Nerve Pain Cream | 150204A-1 | 0.057 |
| Base Cream | 13261-4 | 0.0000 |

The invention claimed is:

1. A transdermal formulation comprising at least one capsaicinoid, at least one 1,4-dialdehyde sesquiterpene, a penetration enhancer comprising tetrahydropiperine, and a transdermal formulation base, wherein the transdermal formulation base comprises:

(a) an aqueous phase comprising water and at least one emulsion stabilizer;
(b) an oil phase comprising at least one emulsifier, at least one emulsion stabilizer, at least one emollient comprising at least one flavonoid, and at least one other emollient;
wherein the oil and aqueous phase form an emulsion;
(c) an external phase comprising at least one flavonoid containing-extract, the at least one penetration enhancer comprising tetrahyropiperine, the at least one capsaicinoid, the at least one 1,4-dialdehyde sesquiterpene, and at least one phospholipid-complexed flavonoid; and optionally
(d) at least one preservative phase.

2. The transdermal formulation of claim 1, wherein the at least one 1,4-dialdehyde sesquiterpene is selected from polygodial, drimanial, isovelleral, warburganal and mixtures thereof.

3. The transdermal formulation of claim 2, wherein the at least one 1,4-dialdehyde sesquiterpene comprises polygodial.

4. The transdermal formulation of claim 1, wherein the transdermal formulation comprises *Tasmannia lanceolata* or Tazmanian Mountain Pepper (TMP), or an extract of *Tasmannia lanceolata* or TMP, as a source of the at least one 1,4-dialdehyde sesquiterpene.

5. The transdermal formulation of claim 4, wherein the source of the at least one 1,4-dialdehyde sesquiterpene is present in the formulation in an amount of about 1% wt % to about 5 wt %, or about 2 wt % to about 4 wt %, of the total formulation.

6. The transdermal formulation of claim 1, wherein the transdermal formulation comprises chili pepper or cayenne pepper, or an extract of chili pepper or cayenne pepper, as a source of the at least one capsaicinoid.

7. The transdermal formulation of claim 6, wherein the source of the at least one capsaicinoid is present in the formulation in an amount of about 0.005% wt % to about 0.5 wt %, or about 0.01 wt % to about 0.1 wt %, of the total formulation.

8. The transdermal formulation of claim 1, wherein the tetrahydropiperine is present in the formulation in an amount of about 0.01% wt % to about 1.0 wt %, or about 0.05 wt % to about 0.5 wt %, of the total formulation.

9. The transdermal formulation of claim 1, wherein the at least one capsaicinoid comprises capsaicin, and wherein the at least one 1,4-dialdehyde sesquiterpene comprises polygodial.

10. The transdermal formulation of claim 9, wherein the transdermal formulation comprises:
chili pepper or cayenne pepper, or an extract of chili pepper or cayenne pepper, as a source of capsaicin; and
*Tasmannia lanceolata* or Tazmanian Mountain Pepper (TMP), or an extract of *Tasmannia lanceolata* or TMP, as a source of polygodial.

11. The transdermal formulation of claim 10, wherein the source of polygodial is TMP or an extract thereof, and the source of capsaicin is cayenne pepper or an extract thereof.

12. The transdermal formulation of claim 1 in the form of a cream, gel, liquid suspension, ointment, solution or patch.

13. The transdermal formulation of claim 1, in the form of a cream.

14. The transdermal formulation of claim 13, wherein the cream has a viscosity of about 50000 cps to about 500000 cps, or about 85000 cps to about 200000 cps as measured using a Brookfield RVT T4 2 RPM instrument at room temperature.

15. The transdermal formulation of claim 1, having improved color characteristics.

16. A method for treating inflammation comprising administering an effective amount of one or more of the formulations according to claim 1 to a subject in need thereof.

17. A method for treating a capsaicinoid-responsive condition comprising administering an effective amount of one or more of the formulations of claim 1 to a subject in need thereof.

18. The method of claim 17, wherein the capsaicinoid-responsive condition is selected from one or more of pain (including painful neuropathies and musculosketal pain), inflammation, itch, psoriasis, pruritis and microbial infections.

19. The method of claim 17, wherein the formulations provide treatment with a lower amount of irritation or burning sensation compared to other transdermal or topical capsaicinoid formulations.

* * * * *